US006383490B1

(12) United States Patent
Wirsching et al.

(10) Patent No.: US 6,383,490 B1
(45) Date of Patent: May 7, 2002

(54) ANTI-COCAINE VACCINE

(75) Inventors: Peter Wirsching, Del Mar; Kim D. Janda, San Diego, both of CA (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 09/077,434

(22) PCT Filed: Dec. 16, 1996

(86) PCT No.: PCT/US96/19982

§ 371 Date: Jun. 12, 1998

§ 102(e) Date: Jun. 12, 1998

(87) PCT Pub. No.: WO97/21451

PCT Pub. Date: Jun. 19, 1997

Related U.S. Application Data

(63) Continuation of application No. PCT/US96/19982, filed on Dec. 16, 1996, which is a continuation-in-part of application No. 08/572,849, filed on Dec. 14, 1995, now abandoned.

(51) Int. Cl.$^7$ ................... A61K 39/395; C07K 14/765; C07K 14/77; C07K 16/44; C12P 21/08
(52) U.S. Cl. ................... 424/193.1; 424/194.1; 424/141.1; 424/75.1; 530/388.9; 530/389.8; 530/403; 530/405; 530/807; 546/23; 546/130; 546/132
(58) Field of Search .................. 530/807, 388.9, 530/389.8, 403, 405; 424/175.1, 193.1, 141.1, 194.1; 546/23, 130, 132

(56) References Cited

U.S. PATENT DOCUMENTS

| | | |
|---|---|---|
| 3,966,744 A | 6/1976 | Goldstein et al. ............ 260/292 |
| 4,123,431 A | * 10/1978 | Soffer et al. |
| 5,233,042 A | 8/1993 | Buechler ..................... 546/129 |
| 5,463,028 A | 10/1995 | Landry et al. ............... 530/405 |
| 5,730,985 A | * 3/1998 | Barber et al. ............. 424/193.1 |
| 5,760,184 A | 6/1998 | Swain et al. .............. 530/387.1 |
| 5,773,003 A | 6/1998 | Swain et al. .............. 424/193.1 |
| 5,840,307 A | 11/1998 | Swain et al. .............. 424/193.1 |
| 5,876,727 A | 3/1999 | Swain et al. .............. 424/193.1 |

OTHER PUBLICATIONS

M. Carrera et al, Nature, vol. 378, pp. 327–330, Dec. 1995.*
M. Carrera et al, Chemical Abstracts 1995: 1004551(HCA-PLUS).*

Bagasra, Omar, et al., "A Potential Vaccine For Cocaine Abuse Prophylaxis," *Immunopharmacology* (1992) vol. 23:173–179.

Basmadijan, Garo P., et al., "Generation Of Polyclonal Catalytic Antibodies Against Cocaine Using Transition State Analogs Of Cocaine Conjugated To Diphtheria Toxoid," *Chem. Pharm. Bull.* (1995) vol. 43, No. (11):1902–1911.

Berkman, Clifford E., et al., "Synthesis Of An Immunogenic Template For The Generation Of Catalytic Antibodies For (−)–Cocaine Hydrolysis," *J. Org. Chem.* (1996) vol. 61:5686–5689.

Chandrakumar, Nizal S., et al., "Phenylphosphonate Monoester Analogs Of Cocaine. Potential Haptens For The Generation Of Catalytic Antibodies," *Bioorganic & Medicinal Chemistry Letters* (1993) vol. 3, No. (2):309–312.

Erlanger, Bernard F., "The Preparation Of Antigenic Hapten–Carrier Conjugates: A Survey," *Methods In Enzymology* (1980) vol. 70:85–104.

Hipert, Reinhold, et al., "Biosensor Technology For The Detection Of Illegal Drugs (∥∥) Antibody Development And Detection Techniques," *Cargo Inspection Technologies* (Jul. 25–27, 1994) vol. 2276:128–136.

Landry, Donald W., et al., "Antibody–Catalyzed Degradation Of Cocaine," *Science* (Mar. 26, 1993) vol. 259 1899–1901.

Rocio, M., et al., "Suppression Of Psychoactive Effects Of Active Cocaine by Active Immunization," *Nature* (Dec. 14, 1995) vol. 378:727–730.

Sakurai, Mitsuya, et al., "Design And Synthesis Of A Cocaine–Diamide Hapten For Vaccine Development," *Tetrahedron Letters* (1996) vol. 37, No. (31):5479–5482.

Yang, G., et al., "Anti–Cocaine Catalytic Antibodies: A Synthetic Approach To Improved Antibody Diversity," *J. Am. Chem Soc.* (1996) vol. 118:5881–5890.

* cited by examiner

*Primary Examiner*—Mary E. Ceperley
(74) *Attorney, Agent, or Firm*—Bret E. Field; Bozicevic, Field & Francis

(57) ABSTRACT

An anti-cocaine vaccine employs a cocaine hapten conjugated to a carrier protein. The anti-cocaine vaccine elicits an immune response which reduces the psychoactive effects of cocaine consumption by the production of anti-cocaine polyclonal antibodies. The antibodies may be employed in an ELISA test for assaying cocaine. The immune response elicited by the anti-cocaine vaccine produces antibody producing cells which may be isolated and cloned for producing anti-cocaine monoclonal antibodies.

28 Claims, 13 Drawing Sheets

ANTI-COCAINE VACCINE

CROSS REFERENCE TO RELATED APPLICATIONS

This application is a continuation of PCT application serial no. PCT/US96/19982 filed on Dec. 16, 1996, which application is a continuation in part of application Ser. No. 08/572,849 filed Dec. 14, 1995, abandoned the disclosures of which applications are herein incorporated by reference.

STATEMENT OF GOVERNMENT RIGHTS

This invention was made with government support under the National Institute of Drug Abuse grant No. DA 08590. The U.S. government has certain rights in the invention.

SPECIFICATION

1. Field of Invention

The invention relates to methods for treating cocaine abuse. More particularly, the invention relates to anti-cocaine vaccines that elicit immune responses for reducing the psychoactive effects of cocaine consumption.

2. Background

Cocaine is a powerfully addictive substance and new strategies are needed to treat its abuse. Cocaine degrades spontaneously in vitro and in vivo (E. R. Garrett, et al., *Journal of Pharmaceutical Science* (1983): vol. 72, p 258–271; D. J. Stewart, et al., *Clin. Pharmacol. Ther.* (1979): vol. 25, p 464–468). A principle route for the degradation of cocaine is the hydrolysis of the methyl ester to produce the nonpsychoactive compound benzoylecgonine (K. A. Cunningham, et al., *Neuropsychopharmacology* (1990): vol 3, p 41–50). Nonspecific esterases are also known to contribute to the in vivo degradation of cocaine through cleavage of both the methyl and benzoate esters (M. R. Brzezinski, et al., *Biochem. Pharmacol.* (1994): vol. 48, p 1747–1755; C. S. Boyer, et al., *J. Pharmacol. Exp. Ther.* (1992): vol. 260, p 939–946; R. A. Dean, et al. *FASEB J.* (1991): vol. 5, p 2735–2739; K. Matsubara, et al., *Forensic Sci. Intl.*(1984): vol. 26, p 169–180; Y. Liu, et al., *J. Chromatography* (1982): vol. 248, p 318–320).

Donald Landry, et al. disclose that catalytic monoclonal antibodies (mAbs) directed to the hydrolysis of cocaine can be elicited by immunization with transition state analogues of cocaine (PCT International Application, WO 9320076 A1, published Oct. 14, 1993 based upon serial number 93-PCT/US 3163, filed Apr. 2, 1993; and Science (1993): vol. 259, p 1899–1901). The catalytic mAbs generated thereby are shown by Landry to catalyze the hydrolysis of cocaine and to reduce cocaine levels in human blood thereby. The catalytic mAbs are further disclosed by Landry to be therapeutically employable for treating cocaine overdose and/or cocaine addiction.

G. P. Basmadjian, et al., disclose that catalytic polyclonal antibodies directed to the hydrolysis of cocaine can be elicited by immunization with transition state analogues of cocaine (Chem. Pharm. Bull. (1995): vol. 43, p 1902–1911). Preliminary results showed that mice immunized with immunoconjugates derived from these analogues produced, in some cases, high titers of serum catalytic antibodies as judged from an in vitro radioassay. No further work has been reported.

S. Spector, et al. disclose that mice can be actively immunized with a morphine immunogen and that serum from such mice contain antibodies that bind dihydromorphine. Morphine effects and the plasma concentration of morphine were shown to be diminished in these immunized mice (S. Spector, et al., Pharmacol. Rev. (1973): vol. 25, p 281–291; and B. Berkowitz, et al., Science (1972): vol. 178, p 1290–1292).

What is needed is an anti-cocaine vaccine for generating an active immunization to cocaine. More particularly, the antibodies generated by the anti-cocaine vaccine should block the actions of the cocaine by preventing the entry of cocaine into the central nervous system. The anti-cocaine vaccine should be characterized by reduced side effects as compared to the side effects associated with treatments based on manipulation of central neurotransmitter function.

SUMMARY OF THE INVENTION

It is disclosed herein that generating an active immunization to cocaine offers a means of blocking the actions of the drug by preventing it from entering the central nervous system. This method of treatment has less side effects than treatments based on manipulation of central neurotransmitter function. The design and preparation of a cocaine immunogen requires special regard for the stability of cocaine both free and as a haptenic determinant. Immunochemistry and a well-defined behavioral paradigm are brought together to address the problem of inactivation of the psychostimulant actions of cocaine. Active immunization is achieved with a novel, stable cocaine conjugate, disclosed below, which suppresses locomotor activity and stereotyped behavior in subjects induced by cocaine but not by amphetamine. Moreover, following acute injection of cocaine, levels of cocaine in the striatum and cerebellum of the immunized subjects are significantly lower than those of control animals. These results demonstrate that immunopharmacotherapy can be employed for treating cocaine abuse.

The design and preparation of a cocaine immunogen requires special attention to the stability of free cocaine in solution and as a haptenic determinant. Cocaine degrades spontaneously in vitro and in vivo. (E. R. Garrett, et al., J. Pharmaceutical Sci. (1983): vol. 72, p 258–271; and D. J. Stewart, et al., Clin. Pharmacol. Ther. (1979): vol. 25, p 464–468. Degradation occurs largely through hydrolysis of the methyl ester to produce the nonpsychoactive compound benzoylecgonine (K. A. Cunningham, et. al., Neuropsychopharmacol.(1990): vol. 3, p 41–50). Nonspecific esterases are also known to contribute to the in vivo degradation of cocaine through cleavage of both the methyl and benzoate esters (M. R. Brzezinski, et. al., Biochem. Pharmacol. (1994): vol. 48, p 1747–1755; C. S. Boyer, et. al., J. Pharmacol. Exp. Ther. (1992): vol. 260, p 939–946; R. A. Dean, et. al. FASEB J. (1991): vol. 5, p 2735–2739; K. Matsubara, et al., Forensic Sci. Intl.(1984): vol. 26, p 169–180; Y. Liu, et. al., J. Chromatography (1982): vol. 248, p 318–320). Conjugates that display epitopes structurally similar to those of metabolites, especially benzoylecgonine, would compromise the avidity and specificity of a cocaine-specific immune response (M. J. Taussig, Current Topics Microbiol. Immunol. (1973): vol. 60, p 125–174; and A. L. Misra, et al., Res. Comm. Che. Path. Pharmacol. (1976): vol. 13, p 579–584). Also, an appreciable benzoylecgonine titer would be exceptionally detrimental since the antiserum would be inadequate in neutralizing cocaine, particularly in the presence of rapidly formed and stable metabolites. Although each retains the phenyl ring as a major recognition element, the neutrality of cocaine contrasts with the negatively charged benzoylecgonine, a factor in antibody binding, making it possible to maximize the affinity and selectivity for cocaine. By joining the carrier protein to the cocaine framework using a linker at the position occupied by the methyl ester, any minor decomposition of the linked hapten results not in a benzoylecgonine response, but primarily in nonhaptenic recognition. Attention to such aspects of the immunochemistry must be emphasized in view of an unsuccessful report of a potential cocaine prophylactic (O. Bagasra, et al., Immunopharmacol.(1992): vol. 23, p 173–179; G. Gallacher, Immunopharmacol (1994): vol. 27, p 79–81). The hapten 4 (compound 4) was synthesized in four steps starting from (–)-cocaine (FIG. 1). The key reaction, alkylation of (–)-ecgonine, introduced the required tether. The stereochemical configuration remained intact at C-2 of the tropane nucleus. This ester linker mimics the alkyl character of the methyl ester of cocaine which is important for recognition of this part of the molecule. Coupling of 4 to keyhole limpet hemocyanin (KLH) afforded the conjugate, 4-KLH, for immunization.

One aspect of the invention is directed to cocaine analogs. Preferred cocaine analogs are represented by the following structures:

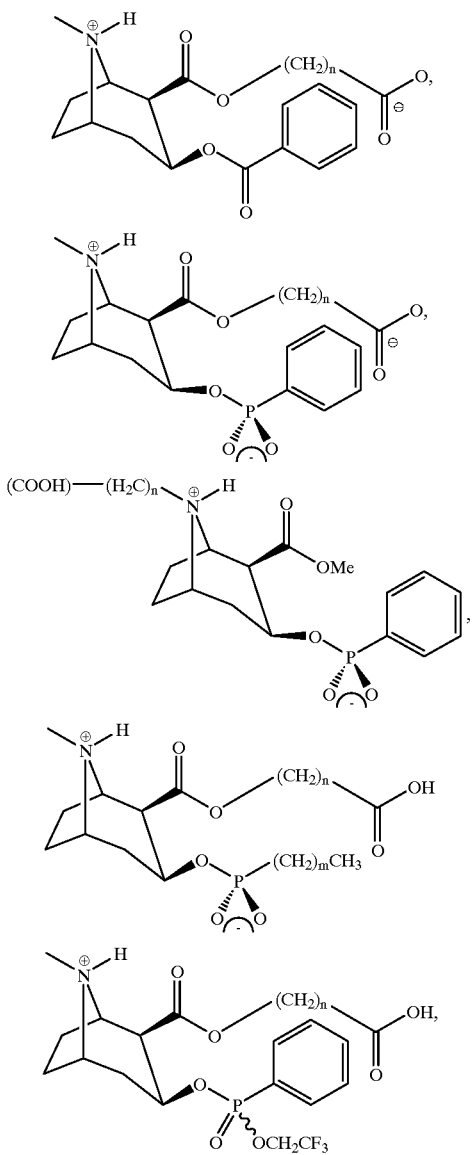

-continued

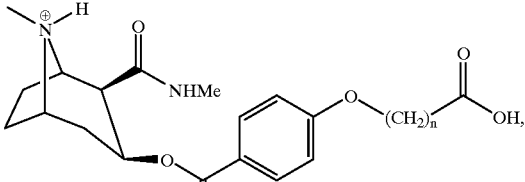

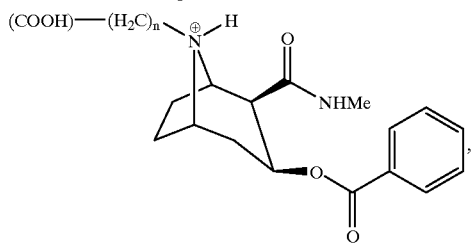

and

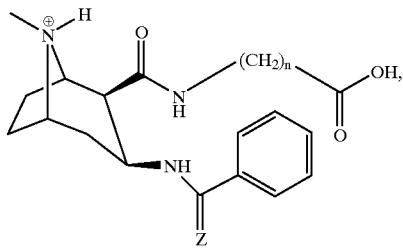

where n is greater than or equal to 2 and less than or equal to 8. In preferred embodiments, n is greater than or equal to 4, less than or equal to 6, or equal to five.

Another aspect of the invention is directed to cocaine immunoconjugates. Preferred cocaine immunoconjugates are represented by the following structure:

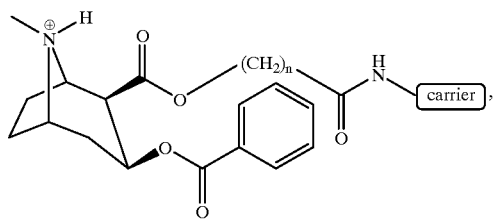

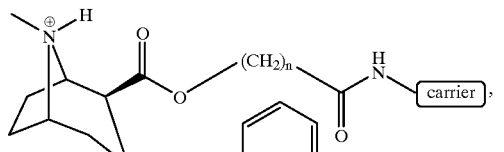

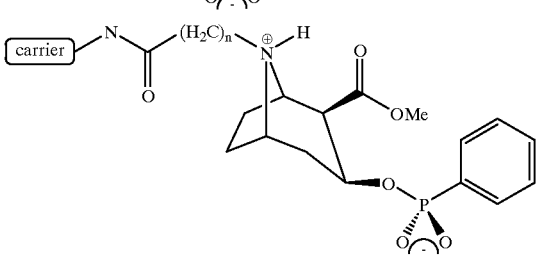

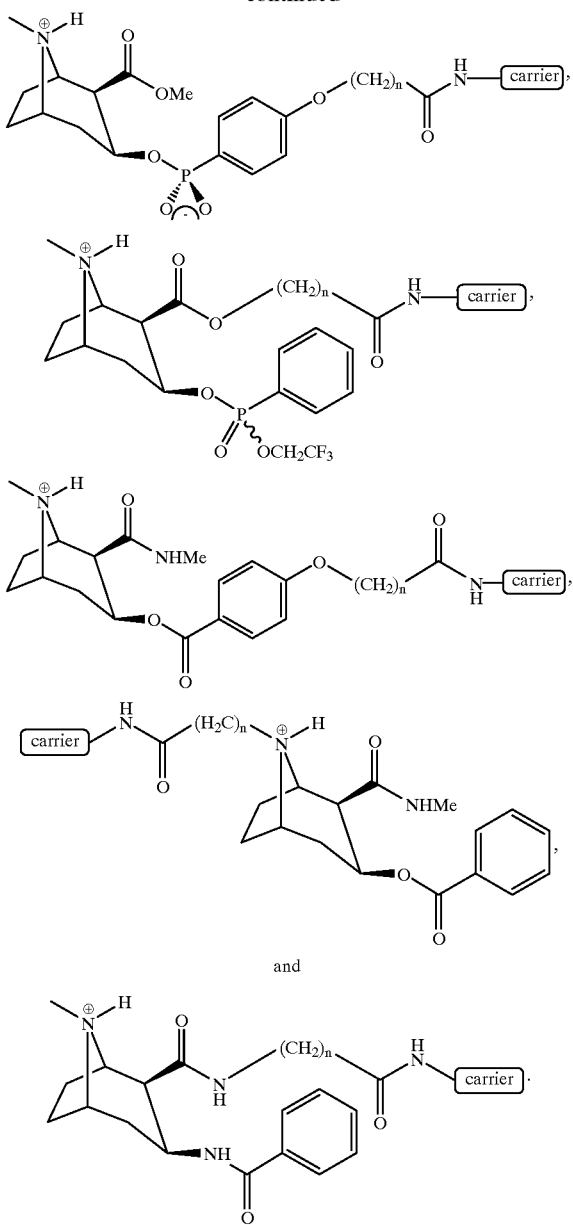

where n is greater than or equal to 2 and less than or equal to 8. In preferred embodiments, n is greater than or equal to 4, less than or equal to 6, or equal to five. An additional preferred cocaine immunoconjugate is represented by the following structure:

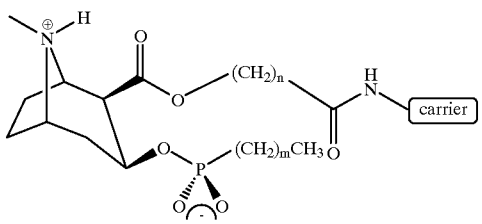

wherein n and m are greater than or equal to 4, less than or equal to 6, or n is six and m is four.

Another aspect of the invention is directed to a method for suppressing psychoactive effects of cocaine within a subject. The method includes a step wherein an anti-cocaine vaccine is administered to the subject. The anti-cocaine vaccine is of a type which includes an injectable sterile solvent and an immunogenic amount of a cocaine immunoconjugate. Preferred immunoconjugates are indicated above.

Another aspect of the invention is directed to an anti-cocaine vaccine. The anti-cocaine vaccine comprises a sterile injectable medium and a cocaine immunoconjugate admixed with said sterile injectable medium. Preferred immunoconjugates are indicated above.

Another aspect of the invention is directed to a method for reducing psychoactive effects displayed by a subject upon administration of cocaine. The method comprises two steps. In the first step, an anti-cocaine immune response is elicited within the subject by vaccination with an anti-cocaine vaccine. The anti-cocaine vaccine includes one of the cocaine immunoconjugates indicated above. In the second step, cocaine is administered to the subject.

Another aspect of the invention is directed to a method for obtaining anti-cocaine polyclonal antibodies. The method includes two steps, an anti-cocaine immune response is elecited within a subject by vaccination with an anti-cocaine vaccine. The anti-cocaine vaccine includes one of the cocaine immunoconjugates indicated above. In the second step, anti-cocaine polyclonal antibodies are isolated from the subject.

Another aspect of the invention is directed to anti-cocaine polyclonal antibodies produced according to the method indicated above.

An other apsect of the invention is directed to a method for obtaining anti-cocaine monoclonal antibodies. The method includes three steps. In the first step, an anti-cocaine immune response is elicited within a subject by vaccination with an anti-cocaine vaccine. The anti-cocaine vaccine includes one of the cocaine immunoconjugates indicated above. In the second step, an antibody producing cell from the subject of said Step A which expresses an anti-cocaine antibody is isolated and cloned. In the third step, anti-cocaine monoclonal antibody expressed by antibody producing cell isolated and cloned in the second step are isolated.

Another aspect of the invention is directed to anti-cocaine monoclonal antibodies produced according to the method indicated above.

DETAILED DESCRIPTION

Conjugation of Cocaine Hapten with Carrier

Figure 1:
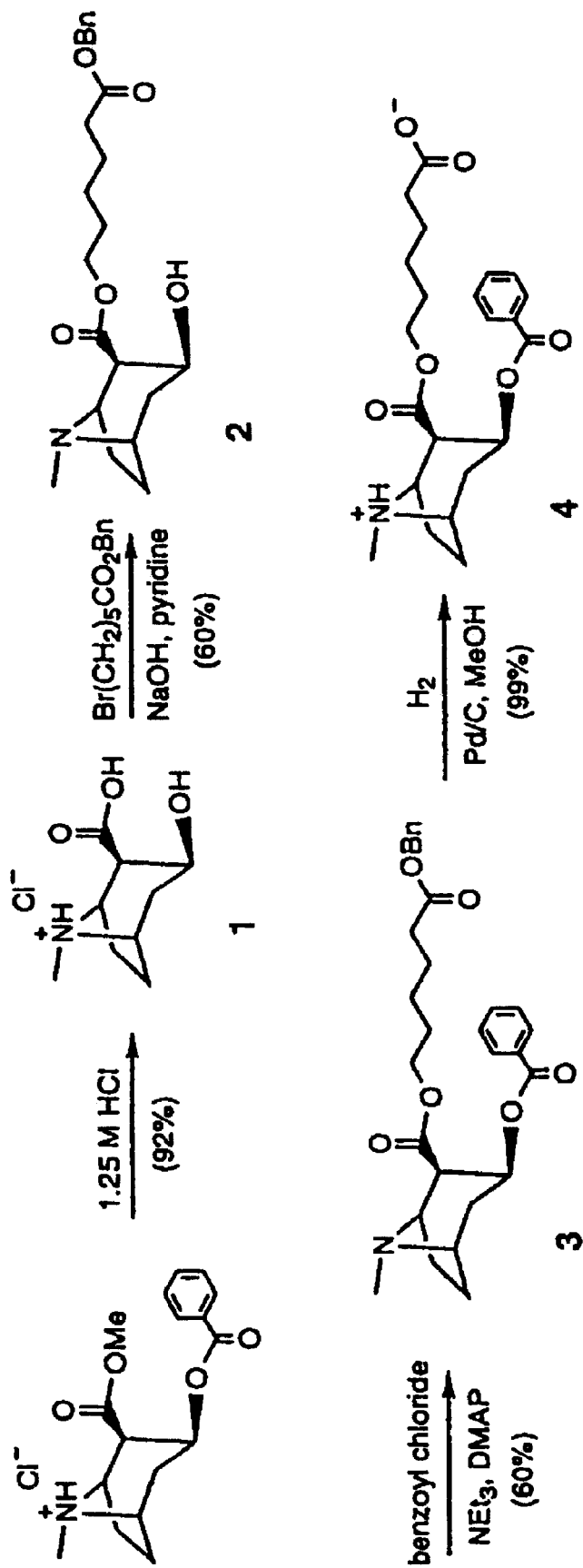
FIG. 1 illustrates a synthetic scheme for making the cocaine hapten 4 employed in the anti-cocaine vaccine.

The immunoconjugate 5 used in the anti-cocaine vaccine was prepared by coupling the hapten 4 with a carrier as described as follows:

Hapten 4 (20 mmol) was activated for coupling in dimethylformamide (DMF) (200 $\mu$l) using an aqueous solution of 1-(3-dimethylaminopropyl)-3-ethyl-carbodiimide (EDC) (26 $\mu$mol) and N-hydroxysulfo-succinimide (sulfo-NHS) (26 $\mu$mol) (Pierce). The aqueous content was 10%. After 20 hours at 22° C. the solution was added to KLH (20 mg) in 4 ml of 50 mM phosphate buffer (PB), pH 7.5. This was kept at 4° C. for 20 hours during which time turbidity developed. The fine suspension was dialyzed against two changes of 100 mM PB, pH 7.0, in which it could be frozen and stored for at least two years. Propionic acid was activated and coupled in an identical fashion. This conjugate served as the KLH control for immunization. The same protocol was used to couple 4 to bovine serum albumin (BSA) affording a nonturbid solution of the conjugate used for ELISA. In addition, both KLH and BSA were modified as above with (carbonyl-14C-benzoyl)-4 to determine the extent of labeling and stability of the conjugate. The number of ligands were 29 and 19, respectively. Both conjugates were completely stable in 100 mM PB, pH 7.4, 22° C. for at least 48 hours.

Competitive binding studies demonstrated that the immune response was highly specific for cocaine. The discrimination was greater than 900-fold versus benzoylecgonine and there was no detectable inhibition of cocaine-binding by ecgonine methyl ester. Consequently, inhibition of cocaine-binding immunoglobulins would not be expected in vivo from these metabolites. The polyclonal antibodies from, such an immune response have also been isolated and purified from serum using standard techniques (E. Harlow and D. Lane, Antibodies: A Laboratory Manual, (Cold Spring Harbor Laboratory, New York, 1988). These immunoglobulins were found to have cocaine-binding characteristics similar to the serum itself.

The KLH immunoconjugates prepared from haptens 4 and 43 were also used to obtain monoclonal antibodies (mAbs) with high affinity and specificity for cocaine. These mAbs were derived from murine subjects according to well-established procedures (E. Harlow and D. Lane, Antibodies: A Laboratory Manual, (Cold Spring Harbor Laboratory, New York, 1988); Peters, J. H. and Baumgarten, H., Eds., Monoclonal Antibodies, Springer-Verlag, New York, 1992). A number of mAbs were found to have binding constants in the submicromolar range and were 10–1000 times more specific for cocaine versus cocaine metabolites.

In further studies, immunoconjugates prepared from haptens 4 and 43 have elicited a competent immune response in murine subjects using different carrier proteins (KLH, BSA) and adjuvants (RIBI, aluminum hydroxide). A number of other methods would likely be feasible.

Carrier Proteins

A small haptenic molecule must first be conjugated to an immunogenic carrier, such as a protein, in order to elicit a competent immune response (Williams, C. A. and Chase, M. W., Eds., Methods in Immunology and Immunochemistry (1967): vol. 1, pp 120–187; G. T. Hermanson, Bioconjugate Techniques, (Academic Press, New York, 1996), pp 419–455). There are several different carrier proteins that can be used for coupling to haptens. The two most commonly used carrier proteins are keyhole limpet hemocyanin (KLH) and bovine serum albumin (BSA). Both of these proteins work well and each has particular utility. KLH, due to its structural features and large size, is highly immunogenic. In addition, KLH generally forms particulate immunoconjugates that may further enhance immunogenicity, but also makes such conjugates less suitable for enzyme-linked immunosorbent assay (ELISA). Hence, it is often the protein of choice for generating an anti-hapten immune response. On the contrary, BSA immunoconjugates are usually soluble and therefore very useful for ELISA. However, BSA conjugates have also been used for immunization in conjunction with a different soluble immunoconjugate that is used in subsequent ELISA screening procedures. Other carrier proteins that are often used for coupling to haptens and find utility for either immunization or ELISA include ovalbumin, rabbit serum albumin, and thyroglobulin. Alternative carriers usually reserved only for immunization purposes include toxoids derived from diphtheria and tetanus.

Coupling of Carrier Proteins to Haptens

The following conditions are exemplary for the coupling of haptens to carrier proteins and are included to illustrate one of many possibilities for coupling of the indicated haptens with carrier proteins. Other activated esters in lieu of (EDC) may be used and include dicyclohexylcarbodiimide (DCC) and 2,5,6-$Cl_3(C_6H_2)COCl$ (Aldrich). Other solvents in lieu of DMF may be used and include acetonitrile, methylene chloride, chloroform, ethylacetate and tetrahydrofuran. Other carrier proteins that are often used for coupling to haptens include ovalbumin, rabbit serum albumin, thyroglobulin and toxoids derived from diphtheria and tetanus. Various pH buffer systems can be used and temperatures and reaction times may vary as indicated, depending upon the hapten and carrier protein combination.

Representative conditions are follows: Hapten 4, 7, 15, 18, 21, 24, 30, 37 or 43 (20 mmol) was activated for coupling in dimethylformamide (DMF; other possible solvents listed above) (200 $\mu$l) using an aqueous solution of 1-(3-dimethylaminopropyl)-3-ethyl-carbodiimide (EDC other possible activated ester reagents listed above) (26 $\mu$mol) and N-hydroxysulfo-succinimide (sulfo-NHS) (26 $\mu$mol) (Pierce; reagent increases yields, but not necessary). The aqueous content was 10% (range 5–15%). After 20 hours at 22° C. (range 15–30° C.) the solution was added to KLH, (20 mg; other possible carrier proteins listed above) in 4 ml of 50 mM phosphate buffer (PB; other buffer systems in same pH range may be used), pH 7.5 (pH range 6.5–8.5). This was kept at 4° C. (range 0° C. to 10° C.) for 20 hours during which time turbidity developed. The fine suspension was dialyzed against two changes of 100 mM PB, pH 7.0, in which it could be frozen and stored for at least two years.

Adjuvants

Despite their large size and multiple epitopes, isolated protein structures, such as immunoconjugates, generally require injection as part of an adjuvant medium in order to elicit a competent primary immune response (Williams, C. A. and Chase, M. W., Eds., Methods in Immunology and Immunochemistry (1967): vol 1, pp 197–209; E. Harlow and D. Lane, Antibodies: A Laboratory Manual, (Cold Spring Harbor Laboratory, New York, 1988), pp 96–97; Peters, J. H. and Baumgarten, H., Eds., Monoclonal Antibodies, (Springer-Verlag, New York, 1992), pp 58–60). Adjuvants induce potent cellular and humoral immune responses to a variety of antigens including carbohydrates, peptides, and proteins and have been valuable in the production of polyclonal and monoclonal antibodies. Freund's adjuvants (water-in-oil emulsions with or without heat-inactivated Mycobacterium tuberculosum) has been the most employed over the years. Recently, the RIBI adjuvant system (RAS) (RIBI Immunochem Research, Inc.) has found widespread use. Another commercially available adjuvant is based on aluminum hydroxide. Such an adjuvant may be most suitable for human use. In this regard, newer methods for achieving adjuvant effects have incorporated antigens into biologically degradable polymers and liposomes (J. Kohn, et al., J. Immunol. Methods (1986): vol. 95, p 31–38; D. Davis, et al., Immunol. Lett. (1983): vol. 14, p 341–348).

Assessment of Efficacy

Figure 2:
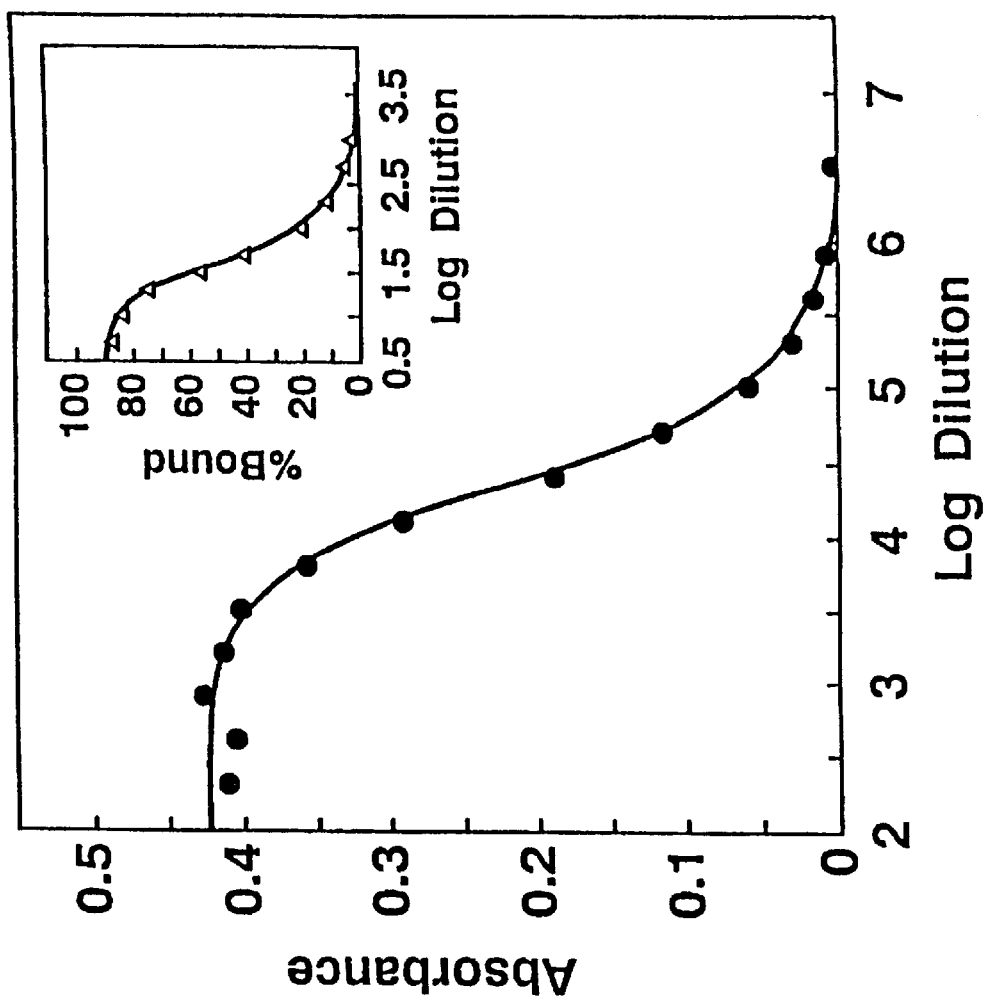
FIG. 2 illustrates analysis of the serum antibodies generated by administration of the anti-cocaine vaccine.
Figure 3:
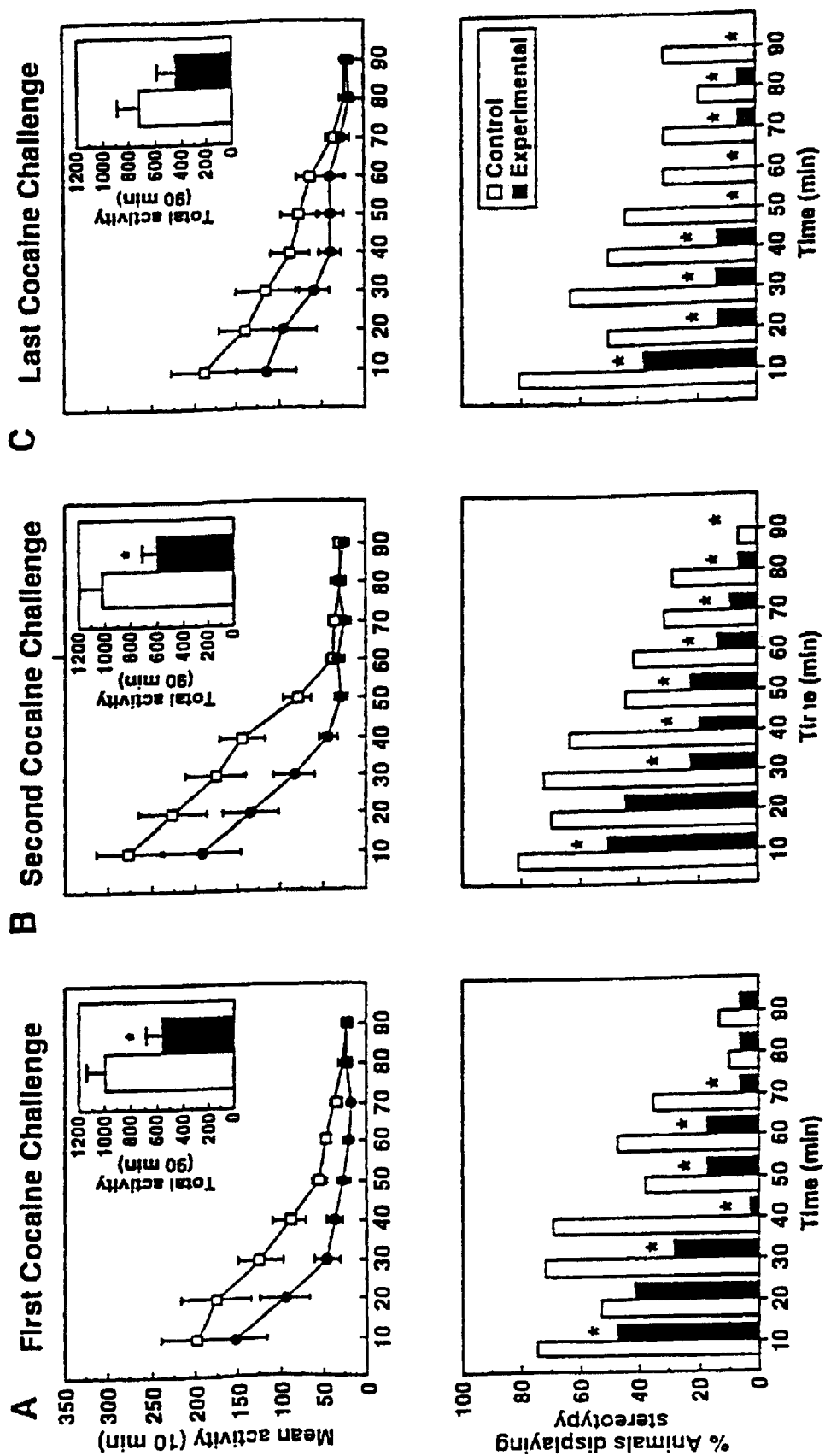
FIG. 3 illustrates the alteration of psychoactive effects resulting from administration of the anti-cocaine vaccine in subjects as compared to subjects not having received the vaccine.

To assess the efficacy of immunization, the psychostimulant effects of cocaine were measured in the rat. This psychostimulant effect is a dose-dependent increase in locomotor activity and stereotyped behavior believed to result from cocaine's actions on dopaminergic neurons in the ventral forebrain and striatum (P. H. Kelly, et al. Eur. J. Pharmacol. (1976): vol. 40,p 45–56.). Male Wistar rats were first tested in photocell cages after treatment with intraperitoneal (i.p.) cocaine-HCl (15 mg/kg) to determine pre-immunization drug response (baseline). This dose of cocaine is an intermediate dose that produces a significant locomotor activation and modest stereotyped behavior. Lower doses produce less locomotor activity and virtually no stereotyped behavior. Higher doses also produce less locomotor activity but more robust stereotyped behavior (M. Lyon, et al., in Current Developments in Psychopharmacology, Essman, W. & Valzelli, L. Eds., (Spectrum, New York, 1975), vol. 2, pp 89–163.). Experimental animals were injected three days later with 4-KLH i.p. as an emulsion in RIBI adjuvant and control animals treated with an emulsion containing only KLH. This primary inoculation was followed by boosts at 21 and 35 days. No stimulation of behavioral activity or other behavioral effects were observed following each immunization, consistent with the inability of the conjugate to cross the blood-brain barrier. Serum samples were assayed 7 days after each boost. Titers were typically 1:24,000 by enzyme-linked immunosorbent assay (ELISA) and 1:50 in a solution radioimmunoassay, as illustrated in FIG. 2. Following the final boost of 4-KLH or KLH, the animals were challenged with systemic cocaine and their locomotor responses and stereotyped behavior were measured (first cocaine challenge). The ambulatory response (crossovers) to cocaine was significantly different between control and immunized animals, as illustrated in FIG. 3. This measure was 42% lower in the experimental group compared to baseline, while the control group displayed a 30% increase compared to baseline. A similar decrease in the psychostimulant actions of cocaine was seen in immunized animals upon two subsequent cocaine challenges with differences in locomotion between groups significant at the time of the first and second challenges, but not the last, as illustrated in FIG. 3. Stereotyped behavior was suppressed in experimental animals consistent with the decreases in locomotor activity and this effect was significant across all challenges, as illustrated in FIG. 3. The antibody titer, as measured seven days prior to the final inoculation, was essentially unchanged eight days following the last challenge.

Analysis of serum immunoglobulin dissociation kinetics, antigen-binding capacity and the effect of antigen dilution (P. Minden, et al., in Handbook of Experimental Immunology. Weir, D. M., Ed., (Davis Co., Philadelphia, 1967), chap. 13, pp. 463–492; M. W. Steward et al., Antibody Affinity: Thermodynamic Aspects and Biological Significance, (CRC Press, Boca Raton, Fla., 1983); H. N. Eisen, in Methods in Medical Research. Eisen, H. N., Ed., (Yearbook Medical Publishers, Chicago, 1964), pp. 106–114; J. H. Hill, et al. Clin. Exp. Immunol. (1973): vol. 15, p 213–224.) were consistent with an in vivo antibody excess having a micromolar average binding constant. In addition, comparison with a purified anti-cocaine murine mAb indicated that one milliliter of undiluted serum from an immunized rat could bind the same amount of cocaine as 4 mg/ml of monoclonal antibody. To complement these experiments, plasma cocaine levels were determined by HPLC according to a modified method of Benuck (M. Benuck, et al., J. Pharmacol. Exp. Ther.(1987): vol. 243, p 144–149) following a 15 mg/kg i.p. injection in a separate group of animals. A measured peak concentration of 5.56±0.31 $\mu$M occurred at 5 minutes which decayed with a half-life of 25 minutes. Taken together, the data suggest that at equilibrium at least 50% of the cocaine present in the blood under physiological conditions is likely to be bound.

Figure 4:
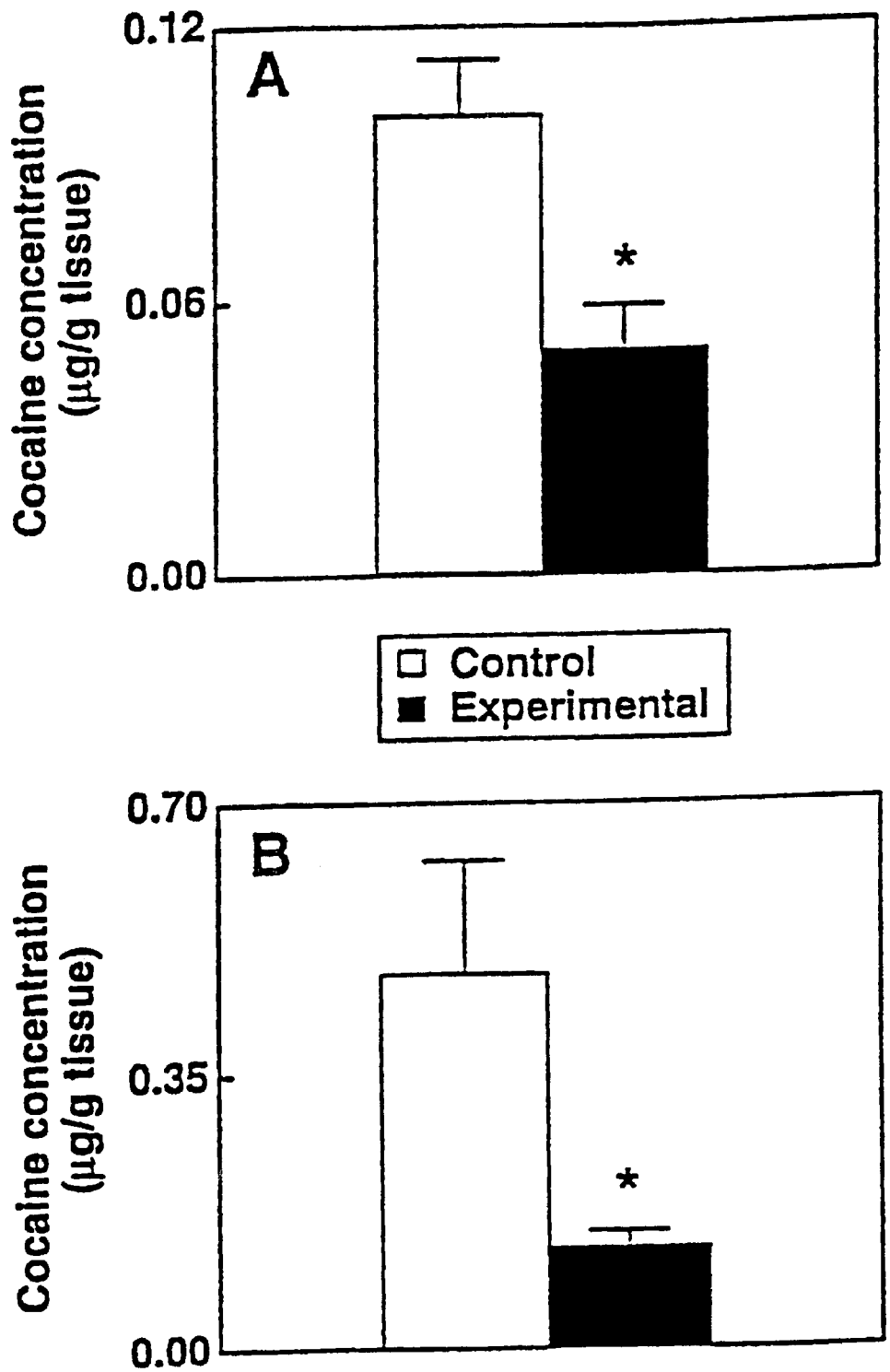
FIG. 4 illustrates the effects of the anti-cocaine vaccine upon levels of cocaine found in the brain of subjects.

To support the hypothesis that the observed psychomotor suppression was specific to cocaine, a second group of animals was immunized as described above, then challenged with amphetamine (0.75 mg/kg) i.p. three days after the last boost. Amphetamine stimulates locomotor activity by facilitating the release of dopamine and, like cocaine, by blocking dopamine uptake. Amphetamine-induced locomotor activity was not significantly different between groups, viz. in one sample, the total crossover counts for controls was 892.35±177.51 while the total for experimentals was 948.75±217.51; $F(1,12)<1$. When these animals were subsequently challenged with cocaine (10 days after the last boost), both measures of locomotor activity were again suppressed in experimental animals as compared with controls, viz., $F(1,12)=14.8$, $P<0.002$. To investigate the basis for this blunted behavioral response, animals were sacrificed thirty minutes after receiving the cocaine injection and their brains extracted for analysis. Levels of cocaine were found to be 52% lower in the striatal tissue and 77% lower in cerebellar tissue of the immunized animals compared to controls, as illustrated in FIG. 4.

In the first group of animals, the reduced psychomotor response observed during the first challenge persisted following subsequent cocaine injections in the experimental group, as illustrated in FIG. 3. At the second cocaine challenge, locomotor activity and stereotyped behavior were significantly decreased in the experimental group as shown in FIG. 3. At the third cocaine challenge, locomotor activity did not differ significantly between the control and experimental groups. However, there continued to be a highly significant difference in the amount of stereotyped behavior. The decrease in stereotyped behavior but not locomotor activity compared to controls may reflect the change in profile of psychomotor stimulation associated with repeated cocaine exposure. Typically, in control animals, repeated administration of cocaine shifts the cocaine dose response to the left (sensitization) and this is reflected in less locomotor activity but more stereotyped behavior (M. Lyon, et al., in Current Developments in Psychopharmacology, Essman, W. and Valzelli, L. Eds., (Spectrum, New York, 1975), vol. 2, pp. 89–163). There was some evidence of an increased psychomotor response and a prolonged stereotyped behavioral response in the control group but this sensitization did not occur in the immunized animals, as illustrated in FIG. 3. However, it is important to emphasize that the overall psychomotor response to cocaine remained dramatically blunted in the immunized animals. These findings suggest that the level of cocaine reaching critical sites of action in the central nervous system of immunized rats was decreased at the time of post-immunization challenges, thus producing a markedly diminished psychomotor effect characteristic of lower doses of cocaine (P. H. Kelly, et al. Eur. J. Pharmacol. (1976): vol. 40,p 45–56). This hypothesis is supported by the maintenance of antibody titer which was the same before the first cocaine challenge and 8 days after the last cocaine challenge, a span of 25 days. Given enough time between cocaine injections, saturation of the immune mechanism may be avoided and protection may be sustained.

Analysis of cocaine concentrations in cerebral tissue revealed considerably lower levels of cocaine in the brains of immunized animals compared to those of controls after cocaine injection. This finding is compatible with the diminished psychostimulant activity observed in the immunized group. Moreover, there is a good correlation between the estimated levels of bound cocaine in the bloodstream and the difference found in the brains of experimental and control animals. In this regard, it seems that extreme antibody affinities are not necessary, but only that they match the peak concentrations of cocaine. It is possible that the thermodynamics of interaction between cocaine binding to antibodies and receptors may be at an optimum (M. C. Ritz, et al., Science (1987): vol. 237, p 1219–1223; M. Fischman, et al., Pharmacol. Biochem. Behav. (1983): vol. 18, p 123–127). In this case, the in vivo immunoglobulin concentration can be a controlling factor in neutralizing the action of the drug. Importantly, the results are an indication that modulation of cocaine levels in the circulation directly influence behavior. This may have implications regarding human administration in that peak plasma concentrations parallel maximum subjective effects (J.Javaid, et al., Science (1978): vol. 202, p 227–228). However, the effects of this type of vaccination protocol on the human condition (i.e. "binge-like" patterns) are difficult to estimate at this time and will require additional study.

Accordingly, it is disclosed herein that the immune-mediated response can be employed to alter reinforcing actions of cocaine in the context of drug dependence subjects. Because immunization therapy would exert its actions outside of the central nervous system, it has none of the side effects of conventional pharmacotherapy. In addition, the protocol disclosed herein can be implemented as a prophylactic treatment and in relapse prevention. Thus, immunopharmacotherapy offers a nontoxic, substance-specific strategy for cocaine abuse treatment that does not affect normal neurochemical physiology.

Analysis of Immune Response

After vaccination with the anti-cocaine vaccine, serum from immunized subjects was tested for production of anti-cocaine antibodies. FIG. 2 illustrates ELISA and radioimmunoassay (see inset) titer measurements of serum from rats immunized with 4-KLH. ELISA plates (96-well) (costar 3590) containing 2.75 ng/well 4-BSA in 50 $\mu$l of 10 mM phosphate buffer/150 mM NaCl (PBS), pH 7.4 were dried overnight at 37° C. This was followed by routine methanol fixing and blocking with blotto (nonfat milk) in PBS. Rat serum was serially diluted beginning with a 1:200 dilution in blotto. Primary antibody (serum) binding was allowed to take place for 1 hour in a moist chamber at 37° C. After washing, 200 ng/well goat anti-rat IgG conjugated with alkaline phosphatase (Southern Biotechnologies Associates, Inc.) in 50 $\mu$l PBS-blotto was added and incubated for 1 hour in a moist chamber at 37° C. The plates were thoroughly washed with water, air dried and developed by adding 100 $\mu$l/well of 200 $\mu$M p-nitrophenylphosphate (Pierce) in 100 mM 4 -morpholinepropanesulfonic acid (MOPS), pH 7.4. After 3 hours at room temperature, the absorbance was measured at 405 nm in a microplate reader (Molecular Dynamics). Radioimmunoassay was conducted in PBS, pH 7.4 in the presence of 5% dimethylsulfoxide (DMSO), 22° C. [3H]-cocaine (specific activity=0.234 Ci/mmol, prepared from norcocaine and [3H]-methyl iodide from Amersham), to give a final concentration of 0.33 $\mu$M, was added to varying dilutions of rat serum, capable of binding more than and less than 50% of the offered counts. The samples were then treated as in the following references, viz. (P. Minden, et al. in Handbook of Experimental Immunology, Weir, D. M. Ed.(Davis Co., Philadelphia, 1967); M. W. Steward, et al., Antibody Affinity: Thermodynamic Aspects and Biological Significance, (CRC Press, Boca Raton, Fla., 1983); H. N. Eisen, in Methods in Medical Research, Eisen, H. N. Ed., (Year Book Medical Publishers, Chicago, 1964); J. H. Hill, et al., Clin. Exp. Immunol. (1973): vol. 15, p 213–224).

Analysis of Psychoactive Effects

An analysis of the psychoactive effects of cocaine administration to rats immunized with the anti-cocaine vaccine is illustrated in FIG. 3. Locomotor activity (crossovers) and stereotyped behavior (sniffing and rearing) following intraperitoneal injection of cocaine post-immunization. Immunizations consisted of a 400 $\mu$l bolus intraperitoneal (i.p.) injection of a RIBI adjuvant (MPL®+TDM) (RIBI Immunochem Research, Inc.) containing approximately 250 $\mu$g 4-KLH or KLH in 100 mM, PB, pH 7.4. The last boost was administered without adjuvant. The figure shows the response to post-immunization cocaine challenge on the third (A), seventh (B), and tenth (C) day following the last immunization boost. Locomotor activity was measured in photocell cages as in described by Gold (L. H. Gold, et al., Pharmacol. Biochem. Behav. (1988): vol. 29, p 645–648). After a 90 minute period of habituation, animals received an i.p. injection of 15 mg/kg cocaine HCl mixed in saline solution (bolus 1 ml/kg) and their locomotor responses measured during a 90 minute session. Based on locomotor activity scores, animals were assigned to the experimental or control group in ranking order. Locomotor data were analyzed by subjecting ten minute total means for locomotor activity to a two-factor analysis of variance (ANOVA) (group×time) with repeated measures on the within-group factor, time. Stereotyped behavior was rated as previously described (J. Fray P. J. et al., Psychopharm. (1980): vol. 69, p 253–259. Data was analyzed by a likelihood ratio method, the "Information statistic" (T. W. Robbins, in Handbook of Psychopharmacology, Iversen, L., Iversen, S. and Snyder, S., Eds., (Plenum, New York, 1977), pp. 37–82; S. Kullback, Information Theory and Statistics, Dover Press, New York, 1968). These figures depict the pooled data from two identical studies for a total of (n=16). At the time of the first cocaine challenge, there was a significant difference between control and experimental groups in both mean activity, viz. (A, top) (control: 987.44±149.5; experimental: 555.07±124.7) $F(1,30)=4.13$; and stereotypy, viz. (A, bottom) $2\hat{I}=85.25$, $df=1, 9$. Both psychomotor measures were again significantly different at the time of the second cocaine challenge, viz. locomotor (B, top) (control: 1035.19±152.92; experimental: 598.25±121.46) $F(1,30)=3.97$, and stereotopy, viz. (B, bottom) $2\hat{I}=94.12$, $df=1,9$. By the last cocaine challenge, locomotor activity did not differ significantly between groups, viz. (C, top) (control: 719.23±133.77; experimental: 443.24±199.50), whereas there was a significant difference in stereotypy, viz. (C, bottom) $2\hat{I}=85.25$, $df=1, 9$; * $P<0.05$, control group different from experimental group.

Measurement of Cocaine Levels in the Brain

FIG. 4 illustrates the measurement of cocaine levels in the brain. Brain cocaine levels 30 minutes after i.p. cocaine injection. Cocaine concentrations were measured by reverse-phase HPLC as described by Benuck (M. Benuck, et al., J. Pharmacol. Exp. Ther.(1987): vol. 243, p 144–149) on brain tissue from animals tested as before (10 days after last boost) except that locomotor activity was tested for only 30 minutes post-injection, at which time they were killed by decapitation. Their brains were rapidly removed and the striata and cerebellum dissected as previously described by Kelly (P. H. Kelly, et al., Brain Research (1975): vol. 94, p 507–522). Immediately following dissection, the striata and cerebellar samples from each animal were weighed, then frozen at −70∞ C. for three days prior to cocaine extraction. Cocaine and its metabolites were extracted from brain tissue as described by Benuck, viz. (M. Benuck, et al., J. Pharmacol. Exp. Ther.(1987): vol. 243, p 144–149). Briefly, approximately 210 mg tissue was sonicated with 300 ml acetonitrile then centrifuged. The supernatant was decanted and cocaine and its metabolites were extracted into 700 ml chloroform/ethanol (4:1) and 70 ml of 0.1 M NaHCO3. Appropriate tissue samples for standards were prepared and analyzed according to the method of Benuck, viz. (Benuck, M., et al., J. Pharmacol. Exp. Ther.(1987): vol. 243, p 144–149). The cocaine levels measured correspond to free cocaine because cocaine-binding antibodies do not cross the blood brain barrier, as evidenced by chromatographic separation and ultraviolet absorption spectra. Data were analyzed by one factor ANOVA. (A) Striatal cocaine concentrations in experimental animals were significantly lower than those of control animals, viz., $F(1,12)=10.37$; $P<0.01$. (B) Cerebellar tissue was sampled to test the generality of cocaine distribution. Cerebellar cocaine concentrations in experimental animals were significantly lower than those of control animals, viz. $F(1,12)=7.30$; $P<0.05$; * $P<0.05$. Data from two animals in the control group were not included in the cocaine-locomotor analysis due to two inadequate cocaine injections which resulted in a seizure (n=1), a limp hindlimb (n=1). Final group size: control (n=6), experimental (n=8).

Production of Monoclonal Antibodies

The anti-cocaine monoclonal antibodies of the present invention are typically produced by immunizing or vaccinating a subject with an inoculum of an anti-cocaine vaccine having a cocaine immunoconjugate as described herein. An anti-cocaine immune response is thus elicited or induced in the subject with the generation of anti-cocaine antibodies. The preparation of antibodies by vaccination with antigenic immunogens is well known in the art and is described in U.S. Pat. Nos. 5,279,956, 5,306,620 and 5,321,123, the disclosures of which are hereby incorporated by reference.

Isolation and cloning of the anti-cocaine antibody producing cells that are generated following immunization procedures described above are achieved in a variety of ways including the preparation of hybridomas as first described by Kohler and Milstein, Nature, 256:495–497 (1975), and further described in U.S. Pat. Nos. 5,279,956, 5,306,620 and 5,321,123, the disclosures of which are hereby incorporated by reference. Alternative exemplary approaches to isolate and clone an anti-cocaine antibody producing cell of the present invention is achieved through the use of recombinant DNA technology with immunological repertoires as described by Orlandi et al., Proc. Natl. Acad. Sci., USA, 86:3833–3837 (1989), Sastry et al., Proc. Natl. Acad. Sci. USA, 86:5728–5732 (1989), Huse et al., Science, 246:1275–1281 (1981) and U.S. Pat. Nos. 4,683, 202 and 5,427,908, the disclosures of which are hereby incorporated by reference. The above-identified references also describe exemplary methods for isolating an anti-cocaine monoclonal antibody expressed by an anti-cocaine antibody producing cell obtained from either classical hybridoma methodologies or by recombinant means. Other methods for obtaining anti-monoclonal antibodies of this invention are also well known in the art.

Synthetic Protocols

The preferred synthetic route for the total synthesis of hapten 4 is illustrated in FIG. 1. Synthesis of hapten 4 involves synthesizing the following intermediates, viz. compounds 1, 2, and 3.

Another aspect of the invention is directed to anti-cocaine vaccines having cocaine immunoconjugates with alternative cocaine haptens, viz. compounds 7, 15, 18, 21, 24, 30, 37, and 43. Each of the alternative cocaine haptens is transformed to its corresponding immunoconjugate by an amide linkage between its linker group and a carrier, as disclosed for immunoconjugate 4.

FIGS. 1 and 5–12 and the protocols below disclose the synthesis of all haptens.

Synthesis of Compound 1, [1R-(exo,exo)]-3-hydroxy-8-methyl-8-azabicyclo[3.2.1]octane-2-carboxylic acid (common name: (−)-ecgonine), as illustrated in FIG. 1

Compound 1. Commercially available (−)-cocaine (Sigma Chemical Co.) was dissolved in 1.25 M HCl (1 g cocaine/12 ml). The mixture was allowed to stir for 16 hours at 110–115° C. (gentle reflux). After cooling to room temperature, the mixture was thoroughly extracted with ether to remove the benzoic acid by-product. The acidic aqueous layer was evaporated on a rotary evaporator under high vacuum and then the residue was redissolved in water and lyophilized to afford a white solid that required no further purification (92% yield).

Synthesis of Compound 2, [1R-(exo,exo)]-6-[[[3-hydroxy-8-methyl-8-azabicyclo[3.2.1]oct-2-yl]carbonyl]oxy]-hexanoic acid phenylmethyl ester, as illustrated in FIG. 1

Compound 2. Compound 1 (2.0 g, 9.0 mmol) was suspended in a mixture of pyridine (250 ml, 3.1 mmol), finely powdered NaOH (760 mg, 19 mmol) and benzyl 6-bromohexanoate (7.8 g, 27 mmol) (synthesized as described below). The mixture was heated to 80° C. and allowed to stir for 20 hours. After cooling to room temperature, the mixture was diluted with 1.25 M HCl (60 ml) and washed with several portions of ether. The ether layer was back-extracted with several portions of 1.25 M HCl. The combined aqueous layers were cooled in an ice bath and diluted with CHCl3 (30 ml). The mixture was stirred and solid K2CO3 was added carefully until pH 9. The phases were separated and the aqueous layer extracted with CHCl3 (3×30 ml) and the combined extracts washed with brine and dried with Na2SO4. The solvent was evaporated leaving a dark brown oil that was triturated with EtOAc. The liquid layer was decanted away from the undesired solid residue. The residue was washed with several portions of EtOAc. The combined EtOAc (150 ml) was dried with Na2SO4 and the solvent evaporated leaving a homogeneous, brown oil (3.8 g). This was purified via flash chromatography (90/10/1 CH2Cl2/MeOH/NH4OH) affording a translucent, light-brown oil (crystallized upon long standing) (2.1 g, 60%). The benzyl 6-bromohexanoate used above was synthesized from 6-bromohexanoic acid (1.0 eq.) (Aldrich Chemical Co.), benzyl alcohol (1.3 eq.), and p-toluenesulphonic acid (0.05 eq.) in refluxing cyclohexane (1.5 ml/mmol 6-Br-hexanoic acid) with the aid of a Dean-Stark trap. After 2 hours, the solution was allowed to cool to room temperature and the solvent removed on a rotary evaporator. The residue was diluted with EtOAc, washed with 1 M NaHCO3, brine, dried with MgSO4 and the solvent evaporated. The residue was distilled (benzyl alcohol forerun) affording a clear, colorless liquid (87% yield) (bp 150–155∞ C., 4 mmHg).

Synthesis of Compound 3, [1R-(exo,exo)]-6-[[[3-(benzoyloxy)-8-methyl-8-azabicyclo[3.2.1]oct-2-yl]carbonyl]oxy]-hexanoic acid phenylmethyl ester, as illustrated in FIG. 1

Compound 3. Compound 2 (250 mg, 0.64 mmol) was dissolved in CH2Cl2 (1.5 ml). The solution was cooled in an ice bath and then NEt3 (107 ul, 0.77 mmol) and DMAP (4-dimethylamino-pyridine) (10 mg, 0.077 mmol) were added. The mixture was allowed to stir at room temperature for 6 hours or until complete, as monitored by TLC. The mixture was diluted with EtOAc and washed with 3.5 M K2CO3, brine, dried with Na2SO4 and the solvent evaporated. The residue was purified via flash chromatography (95/5/1 CH2Cl2/MeOH/NH4OH) affording a thick, straw-colored oil (190 mg, 60%).

Synthesis of Compound 4, [1R-(exo,exo)]-6-[[[3-(benzoyloxy)-8-methyl-8-azabicyclo[3.2.1]oct-2-yl]carbonyl]oxy]-hexanoic acid, as illustrated in FIG. 1

Compound 4. To a solution of compound 3 (136 mg, 0.275 mmol) in MeOH (3 ml) was added 10% Pd/C (30 mg). The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%).

Figure 5:
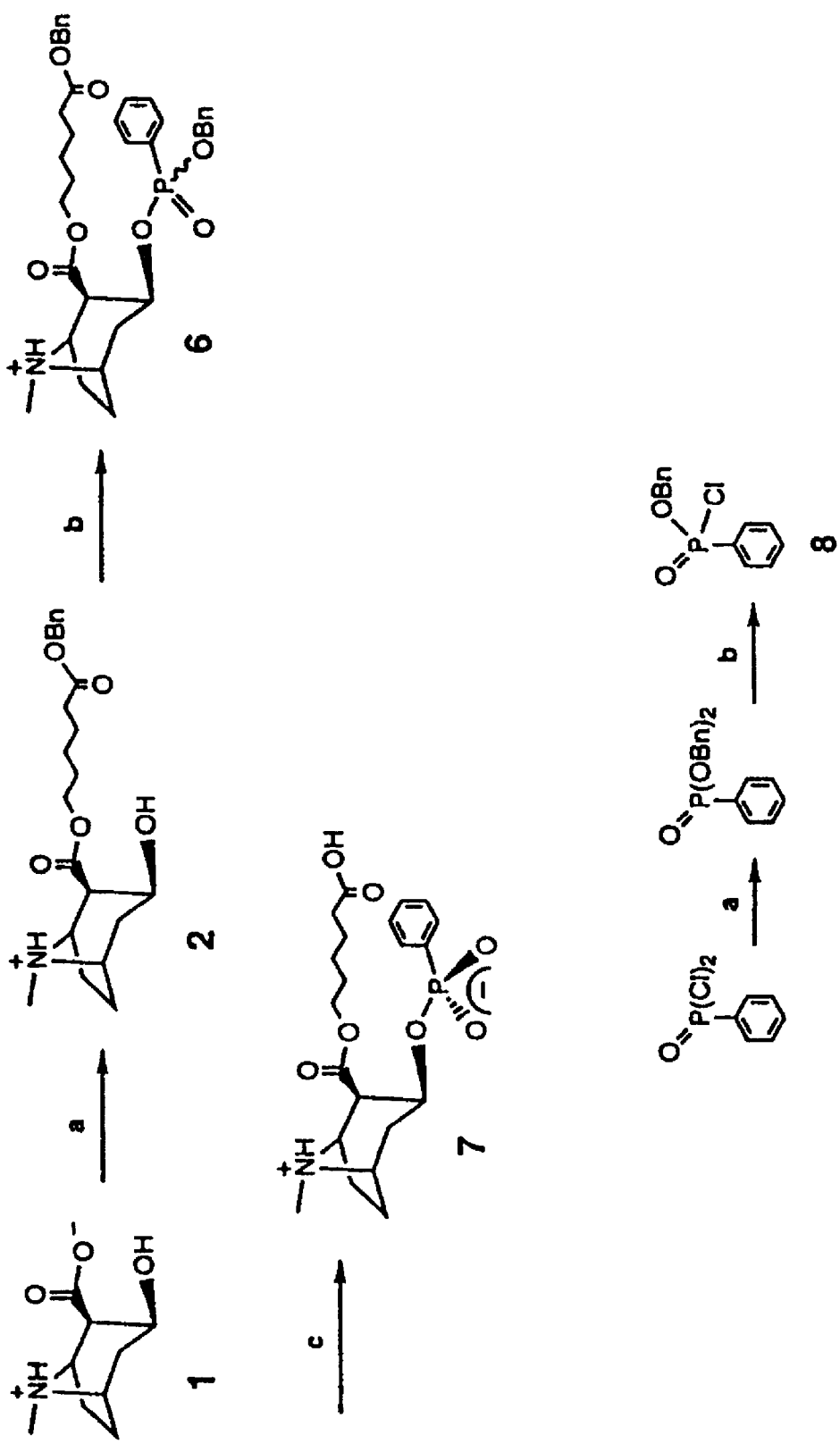
FIG. 5 illustrates the synthesis of hapten 7 using the following steps; top scheme: a) $Br(CH_2)_5CO_2Bn$, NaOH, pyridine; b) (i) LDA, (ii) add 8; c) $H_2$, Pd/C; lower scheme illustrates the synthesis of compound 8 using the following steps: a) benzyl alcohol, $NEt_3$; b) $PCl_5$.

Synthesis of Compound 6 (FIG. 5; Step b)

Compound 6. Compound 2 (1.0 eq.) was dissolved in THF (1 ml/0.5 mmol 2) and the solution cooled in an ice bath. An ice-cold solution of LDA (lithium diisopropylamide) (1.0 eq.) (Aldrich) in THF was added. After 5 minutes, a solution of freshly-prepared compound 8 (1.5 eq.) in THF (1 ml/mmol 8) was added. The ice bath was removed and the mixture stirred at room temperature for 6 hours. After dilution with EtOAc and the usual workup (see compound 3), the crude residue was purified via flash chromatography (95/5/1 EtOAc/MeOH/NH4OH) affording a thick, straw-colored oil (45% yield) as a 50/50 mixture of two diastereomers that did not require separation for the following step.

Synthesis of Compound 7 (FIG. 5; Step c)

Compound 7. To a solution of compound 6 (136 mg, 0.275 mmol) in MeOH (3 ml) was added 10% Pd/C (30 mg). The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%). The compound was obtained as a colorless, glassy solid (99% yield).

Synthesis of Compound 8 (FIG. 5; Steps a–b)

Compound 8. A solution of phenylphosphonic dichloride (1.0 eq.) (Aldrich) in CH2Cl2 (2 ml/mmol) was cooled in an ice bath. A solution of benzyl alcohol (2.0 eq.) and NEt3 (2.1 eq.) in CH2Cl2 (0.2 ml/mmol) was added dropwise. After stirring 16 hours at room temperature, the mixture was diluted with EtOAc and washed with 1 M HCl, 1 M NaHCO3, brine, dried with Na2SO4 and the solvent evaporated. The residue was purified via flash chromatography (70/30 EtOAc/hexane) affording a white solid (84% yield). This material was converted to the phosphonyl chloride immediately before use as follows. To a solution of the dibenzyl ester (1.0 eq.) in CHCl3 (1 ml/mmol) was added PCl5 (1.0 eq.) (Aldrich). The mixture was heated to 45° C. in an oil bath. After 3 hours, the solution was allowed to cool to room temperature and then purged with SO2 gas (generated by heating NaHSO3) for several minutes. The solvent was evaporated and the residue thoroughly dried under high vacuum at 45∞ C. for 30 minutes affording a thick, yellow oil (98% yield).

Figure 6:
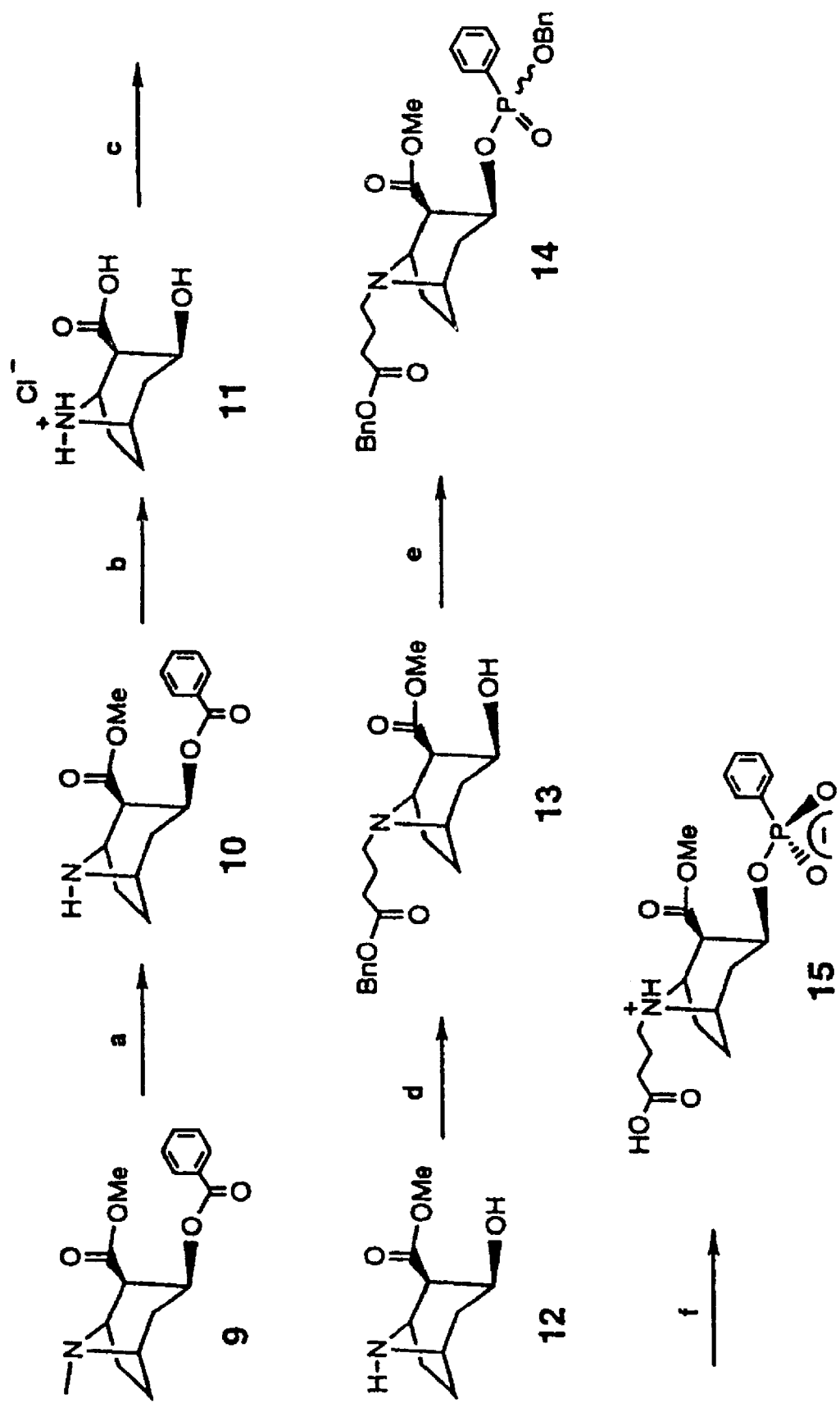
FIG. 6 illustrates the synthesis of hapten 15 using the following steps: a) (i) trichloroethyl chloroformate, (ii) Zn, formic acid; b) 1.25 M HCl, reflux; c) MeOH, HCl; d) $Br(CH_2)_3CO_2Bn$, $NEt_3$; e) (i) LDA, (ii) add 8; f) $H_2$, Pd/C.

Synthesis of Compound 9 (FIG. 6)

Compound 9. Compound 9 is commercially available as (−) cocaine HCl (Sigma). The free-base was prepared from this material using a standard methodology of expedient chloroform extraction from a basic (pH 9–10) (K2CO3) aqueous solution.

Synthesis of Compound 10 (FIG. 6; Step a)

Compound 10. To a solution of compound 9 (1.0 eq.) in benzene (2.5 ml/mmol 9) was added a solution of trichloroethyl chloroformate (1.3 eq.) (Aldrich) in benzene (0.5 ml/mmol). The solution was refluxed for 18 hours. The mixture was cooled in an ice bath and formic acid (0.5 eq.) was added and after 30 minutes NEt3 (0.3 eq.) was added. After stirring 1 hour, water (4 ml/mmol) was added and the mixture extracted thoroughly with ether. The ether extracts were washed with 6 M HCl, dried and evaporated affording the intermediate carbamate as a thick, colorless oil (80% yield). The oil was dissolved in DMF (1.5 ml/mmol) and the solution cooled in an ice bath. Formic acid (2.5 eq.) was added and then activated zinc dust (3.5 eq.) was added in portions over 10 minutes. After 15 minutes, the ice bath was removed and the mixture stirred at room temperature for 18 hours. The mixture was filtered onto crushed ice washing with small portions of DMF. After the ice melted, the yellowish mixture was cooled in an ice bath and acidified with concentrated HCl until pH 2. The cold mixture was extracted with ether and the aqueous layer cooled in an ice bath and made basic with NH4OH to pH 9. The cold mixture was thoroughly extracted with ether, and the combined extracts washed with brine, dried and evaporated affording a thick, pale-yellow oil (41% yield) that required no further purification.

Synthesis of Compound 11 (FIG. 6; Step b)

Compound 11. Compound 10 was dissolved in 1.25 M HCl (4 ml/mmol 10). The mixture was allowed to stir for 20 hours at 110–115° C. (gentle reflux). After cooling to room temperature, the mixture was thoroughly extracted with ether to remove the benzoic acid by-product. The acidic aqueous layer was evaporated on a rotary evaporator under high vacuum and then the residue was redissolved in water and lyophillized affording a white, very hygroscopic solid that required no further purification (98% yield).

Synthesis of Compound 12 (FIG. 6; Step c)

Compound 12. Compound 11 was dissolved in MeOH (5 ml/mmol 11) and the solution thoroughly purged with HCl gas. The reaction flask was sealed and the solution stirred for 18 hours at room temperature and then refluxed for 5 hours. The solvent was evaporated and the hygroscopic HCl salt was converted to the free base (see compound 9) affording a clear, straw-colored oil (78% yield) that crystallized upon prolonged standing.

Synthesis of Compound 13 (FIG. 6; Step d)

Compound 13. Compound 12 (1.0 eq.) was dissolved in CH3CN (4 ml/mmol 12). NEt3 (1.2 eq.), benzyl 4-bromobutanoate (1.2 eq.) (prepared in a similar fashion to the hexanoate, see compound 2) and tetrabutyl-ammoniumiodide (0.1 eq.) were then added. The mixture was heated at 50° C. for 24 hours. After dilution with EtOAc and the usual workup (see compound 3), the crude residue was purified via flash chromatography (95/5/1 EtOAc/MeOH/NH4OH) affording a clear, straw-colored oil (58% yield).

Synthesis of Compound 14 (FIG. 6; Step e)

Compound 14. Compound 13 (1.0 eq.) was dissolved in THF (1 ml/0.5 mmol 2) and the solution cooled in an ice bath. An ice-cold solution of LDA (lithium diisopropylamide) (1.0 eq.) (Aldrich) in THF was added. After 5 minutes, a solution of freshly-prepared compound 8 (1.5 eq.) in THF (1 ml/mmol 8) was added. The ice bath was removed and the mixture stirred at room temperature for 6 hours. After dilution with EtOAc and the usual workup (see compound 3), the crude residue was purified via flash chromatography (95/5/1 EtOAc/MeOH/NH4OH) affording a thick, straw-colored oil (45% yield) as a 50/50 mixture of two diastereomers that did not require separation for the following step. The compound was obtained after flash chromatography (95/5 EtOAc/MeOH) as a clear, straw-colored oil composed of a 50/50 mixture of two diastereomers (40% yield).

Synthesis of Compound 15 (FIG. 6; Step f)

Compound 15. To a solution of compound 14 (136 mg, 0.275 mmol) in MeOH (3 ml) was added 10% Pd/C (30 mg). The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%). The compound was obtained as colorless, hygroscopic crystals (99% yield).

Figure 7:
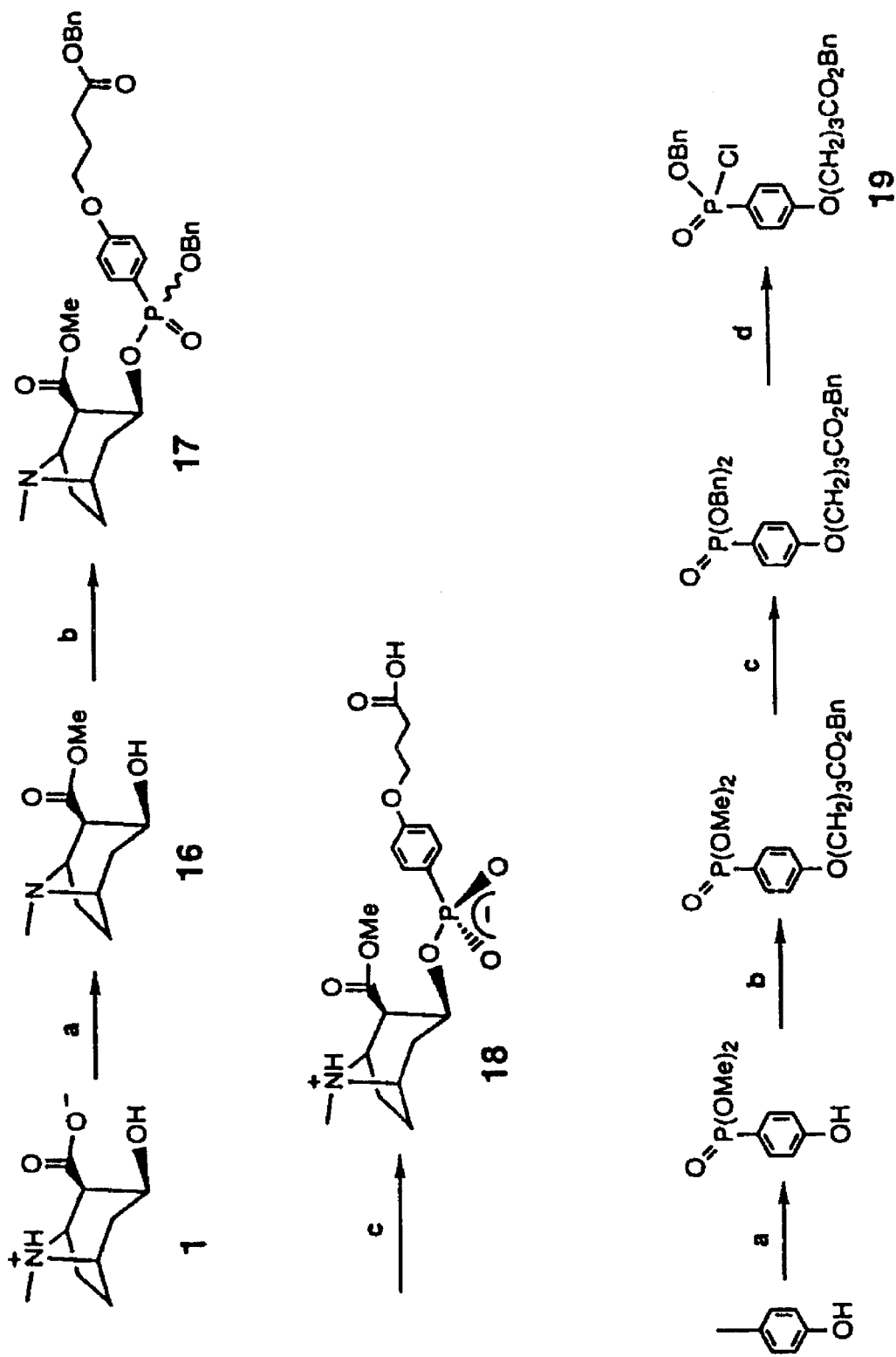
FIG. 7 illustrates the synthesis of hapten 18 using the following steps; top scheme: a) (i) MeOH, HCl, (ii) free-base; b) (i) LDA, (ii) add 19; c) $H_2$, Pd/C; lower scheme illustrates the synthesis of compound 19 using the following steps: a) $P(OMe)_3$, light; b) (i) NaH, (ii) $Br(CH_2)_3CO_2Bn$; c) (i) TMSBr, (ii) oxalyl chloride, (iii) benzyl alcohol, $NEt_3$; d) $PCl_5$.

Synthesis of Compound 16 (FIG. 7; Step a)

Compound 16. Compound 1 was dissolved in MeOH (5 ml/mmol 11) and the solution thoroughly purged with HCl gas. The reaction flask was sealed and the solution stirred for 18 hours at room temperature and then refluxed for 5 hours. The solvent was evaporated and the hygroscopic HCl salt was converted to the free base (see compound 9) affording a clear, straw-colored oil (78% yield) that crystallized upon prolonged standing. The compound was obtained as a clear, colorless oil (78% yield) that crystallized upon prolonged standing.

Synthesis of Compound 17 (FIG. 7; Step b)

Compound 17. Compound 16 (1.0 eq.) was dissolved in THF (1 ml/0.5 mmol 2) and the solution cooled in an ice bath. An ice-cold solution of LDA (lithium diisopropylamide) (1.0 eq.) (Aldrich) in THF was added. After 5 minutes, a solution of freshly-prepared compound 8 (1.5 eq.) in THF (1 ml/mmol 8) was added. The ice bath was removed and the mixture stirred at room temperature for 6 hours. After dilution with EtOAc and the usual workup (see compound 3), the crude residue was purified via flash chromatography (95/5/1 EtOAc/MeOH/NH4OH) affording a thick, straw-colored oil (45% yield) as a 50/50 mixture of two diastereomers that did not require separation for the following step. The compound was obtained after flash chromatography (95/5/1 EtOAc/MeOH/NH4OH) as a pale-yellow oil composed of a 50/50 mixture of two diastereomers (31% yield).

Synthesis of Compound 18 (FIG. 7; Step c)

Compound 18. To a solution of compound 17 (136 mg, 0.275 mmol) in MeOH (3 ml) was added 10% Pd/C (30 mg). The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%). The compound was obtained as colorless, hygroscopic crystals (99% yield).

Synthesis of Compound 19 (FIG. 7; Steps a–e)

Compound 19. Step a: A water-jacketed photochemical reactor (250 ml capacity) (Ace Glass Co.) was charged with a stirring bar, 4-iodophenol (71 g, 0.322 mol) (Aldrich) and trimethyl phosphite (200 g, 1.61 mol) (Aldrich). The solution was purged with nitrogen and cooled with 50/50 water/ethylene glycol (−2° C.) using a circulating bath (Lauda). A water-jacketed high-pressure mercury lamp (Hanovia) was put in place and the entire apparatus wrapped with aluminum foil. The solution was irradiated for 24 hours under nitrogen. The excess trimethyl phosphite was then removed via distillation leaving a residue that contained 60% of the desired product and 40% dimethyl methylphosphonate. The latter was removed via distillation under high vacuum leaving a thick syrup (80 g). This material was purified in portions via flash chromatography (95/5 EtOAc/MeOH) affording a thick, pale-yellow oil (52 g, 80%). Step b: The compound from step a (1.0 eq.) was dissolved in DMF (0.5 ml/mmol) and added dropwise to a stirring, ice-cold suspension of oil-free NaH (1.1 eq.) in DMF (1 ml/mmol). After 15 minutes, benzyl 4-bromobutanoate (1.1 eq.) (see compound 13) was added followed by tetrabutylammoniumiodide (0.011 eq.). The ice bath was removed and the mixture stirred for 2 hours at room temperature. EtOAc was added and the mixture washed thoroughly with brine, dried with Na2SO4, and solvent evaporated. The residue was purified via flash chromatography (EtOAc) affording a pale-yellow liquid (69% yield). Step c: The compound from step b (1.0 eq.) was dissolved in CH2Cl2 (1 ml/mmol) and then trimethylsilylbromide (2.2 eq.) was slowly added. The solution was stirred at room temperature for 2 hours. The solvent mixture was evaporated under reduced pressure and the residue redissolved in CH2Cl2 (1 ml/mmol) containing a drop of DMF and then oxalyl chloride was slowly added. The solution was stirred at room temperature for 1 hour. The solvent mixture was evaporated under reduced pressure and the residue redissolved in CH2Cl2 (2 ml/mmol) and cooled in an ice bath. A solution of benzyl alcohol (2.1 eq.) and NEt3 (2.2 eq.) in CH2Cl2 (0.2 ml/mmol) was then added. The ice bath was removed and the mixture stirred for 18 hours at room temperature. After dilution with EtOAc, the mixture was washed with 1 M HCl, 1 NaHCO3, brine, dried with Na2SO4 and the solvent evaporated. The residue was purified via flash chromatography (50/50 EtOAc/hexane) affording a clear, pale-yellow liquid (60% yield). Step d: The compound from step c was used to prepare compound 19 (99% yield) (see procedure for compound 8).

Figure 8:
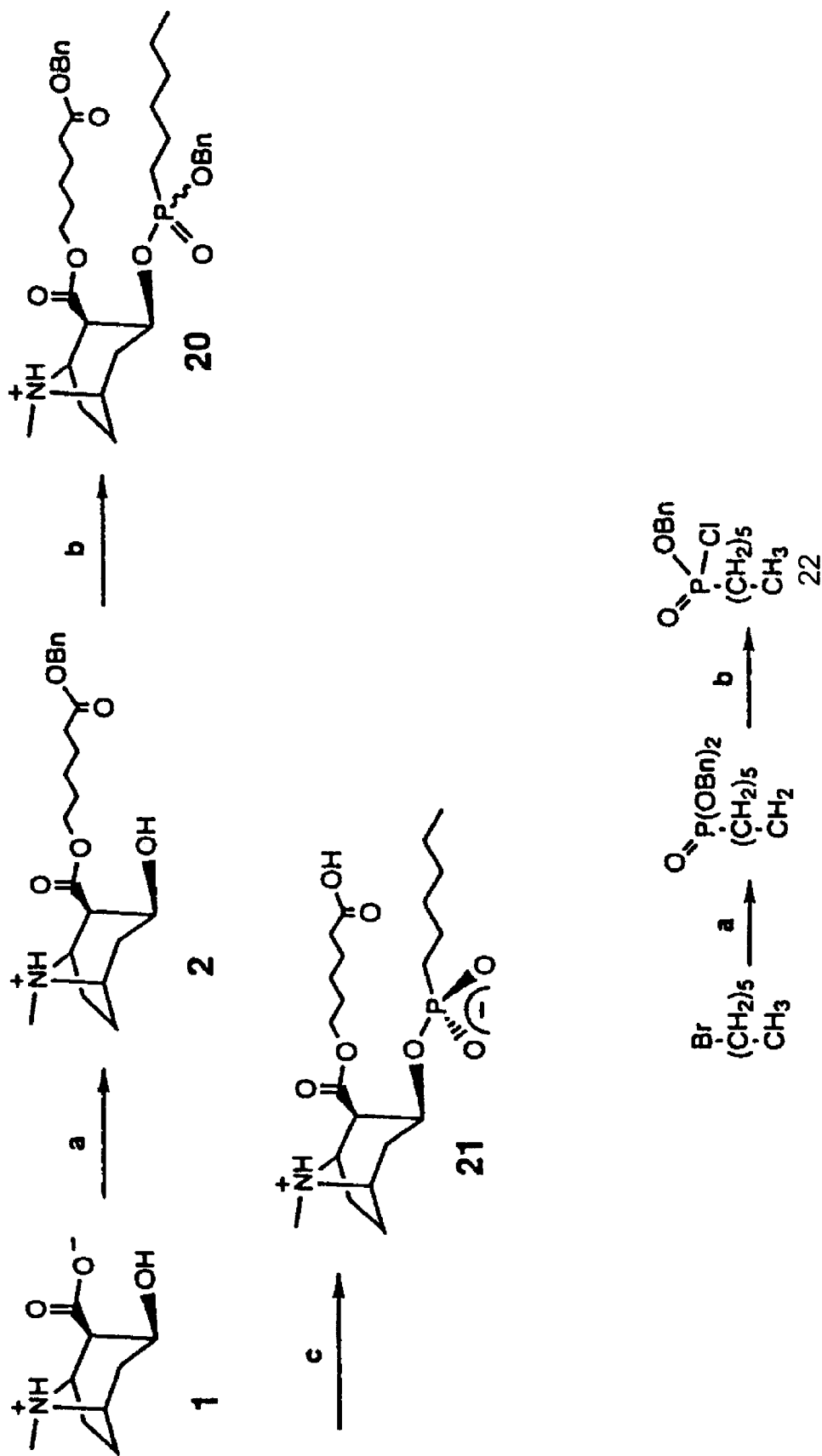
FIG. 8 illustrates the synthesis of hapten 21 using the following steps; top scheme: a) $Br(CH_2)_5CO_2Bn$, NaOH, pyridine; b) (i) LDA, then 22; c) $H_2$, Pd/C; lower scheme illustrates the synthesis of compound 22 using the following steps: a) dibenzyl phosphite, NaH; b) PCl5.

Synthesis of Compound 20 (FIG. 8; Step b)

Compound 20. Compound 2 (1.0 eq.) was dissolved in THF (1 ml/0.5 mmol 2) and the solution cooled in an ice bath. An ice-cold solution of LDA (lithium diisopropylamide) (1.0 eq.) (Aldrich) in THF was added. After 5 minutes, a solution of freshly-prepared compound 8 (1.5 eq.) in THF (1 ml/mmol 8) was added. The ice bath was removed and the mixture stirred at room temperature for 6 hours. After dilution with EtOAc and the usual workup (see compound 3), the crude residue was purified via flash chromatography (95/5/1 EtOAc/MeOH/NH4OH) affording a thick, straw-colored oil (45% yield) as a 50/50 mixture of two diastereomers that did not require separation for the following step. Step a: A solution of dibenzylphosphite (1.0 eq.) (Aldrich) in DMF (1 ml/mmol) was added dropwise to a stirring, ice-cold suspension of oil-free NaH (1.1 eq.) in DMF (1 ml/mmol). After 15 minutes, bromohexane (1.1 eq.) (Aldrich) was added followed by tetrabutylammonium-iodide (0.011 eq.). The ice bath was removed and the mixture stirred for 2 hours at room temperature. EtOAc was added and the mixture washed thoroughly with brine, dried with Na2SO4, and the solvent evaporated. The residue was purified via flash chromatography (80/20 CH2Cl2/EtOAc) affording a clear oil (52% yield). Step b: The compound from step a was used to prepare compound 22 (99% yield) (see procedure for compound 8). The compound was obtained after flash chromatography (90/10 EtOAc/MeOH) as a clear, straw-colored oil composed of a 50/50 mixture of two diastereomers (30% yield).

Synthesis of Compound 21 (FIG. 8; Step c)

Compound 21. To a solution of compound 20 (136 mg, 0.275 mmol) in MeOH (3 ml) was added 10% Pd/C (30 mg). The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%). The compound was obtained as colorless, hygroscopic crystals (99% yield).

Synthesis of Compound 22 (FIG. 8; Steps a–b)

Compound 22. Step a: A solution of dibenzylphosphite (1.0 eq.) (Aldrich) in DMF (1 ml/mmol) was added dropwise to a stirring, ice-cold suspension of oil-free NaH (1.1 eq.) in DMF (1 ml/mmol). After 15 minutes, bromohexane (1.1 eq.) (Aldrich) was added followed by tetrabutylammonium-iodide (0.011 eq.). The ice bath was removed and the mixture stirred for 2 hours at room temperature. EtOAc was added and the mixture washed thoroughly with brine, dried with Na2SO4, and the solvent evaporated. The residue was purified via flash chromatography (80/20 CH2Cl2/EtOAc) affording a clear oil (52% yield). Step b: The compound from step a was used to prepare compound 22 (99% yield) (see procedure for compound 8).

Figure 9:
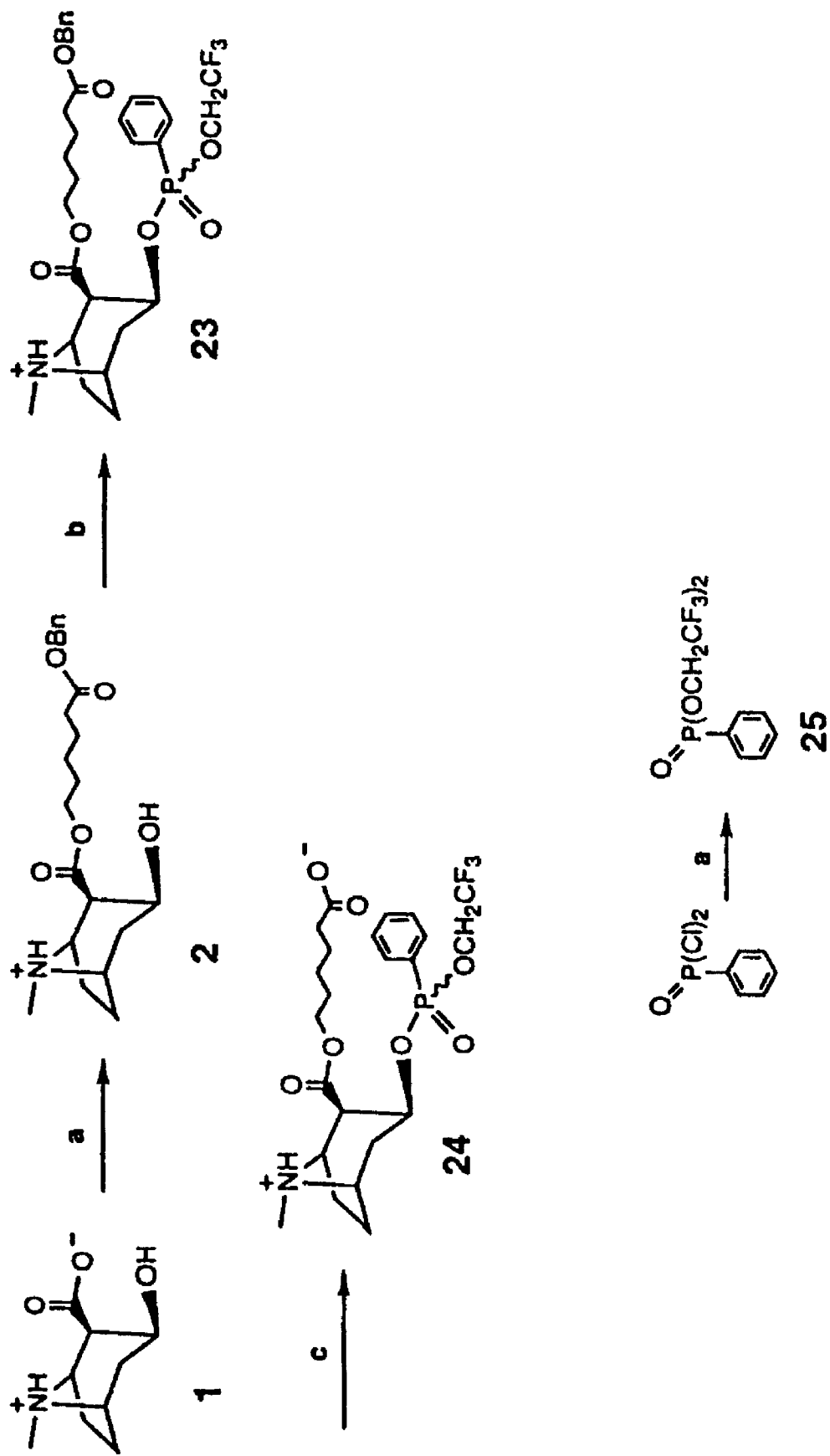
FIG. 9 illustrates the synthesis of hapten 24 using the following steps; top scheme: a) $Br(CH_2)_5CO_2Bn$, NaOH, pyridine; b) (i) LDA, (ii) add 25; c) $H_2$, Pd/C; lower scheme illustrates the synthesis of compound 25 using the following steps: a) trifluoroethanol, $NEt_3$.

Synthesis of Compound 23 (FIG. 9; Step b)

Compound 23. Compound 2 (1.0 eq.) was dissolved in THF (1 ml/0.5 mmol 2) and the solution cooled in an ice bath. An ice-cold solution of LDA (lithium diisopropylamide) (1.0 eq.) (Aldrich) in THF was added. After 5 minutes, a solution of freshly-prepared compound 8 (1.5 eq.) in THF (1 ml/mmol 8) was added. The ice bath was removed and the mixture stirred at room temperature for 6 hours. After dilution with EtOAc and the usual workup (see compound 3), the crude residue was purified via flash chromatography (95/5/1 EtOAc/MeOH/NH4OH) affording a thick, straw-colored oil (45% yield) as a 50/50 mixture of two diastereomers that did not require separation for the following step. The compound was obtained after flash chromatography (90/10 EtOAc/MeOH) as a clear, straw-colored oil composed of 50/50 mixture of two diastereomers (34% yield). A solution of phenylphosphonic dichloride (1.0 eq.) (Aldrich) in CH2Cl2 (2 ml/mmol) was cooled in an ice bath. A solution of trifluoroethanol (2.2 eq.) and NEt3 (2.5 eq.) in CH2Cl2 (0.2 ml/mmol) was added dropwise. After stirring 6 hours at room temperature, the mixture was diluted with EtOAc and washed with 1 M HCl, 1 M NaHCO3, brine, dried with Na2SO4 and the solvent evaporated. The residue was purified via flash chromatography (CH2Cl2) affording a colorless oil (88% yield).

Synthesis of Compound 24 (FIG. 9, Step c)

Compound 24. To a solution of compound 23 (136 mg, 0.275 mmol) in MeOH (3 ml) was added 10% Pd/C (30 mg).

The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%). The compound was obtained as colorless, hygroscopic crystals (99% yield).

Synthesis of Compound 25 (FIG. 9, Step a)

Compound 25. A solution of phenylphosphonic dichloride (1.0 eq.) (Aldrich) in CH2Cl2 (2 ml/mmol) was cooled in an ice bath. A solution of trifluoroethanol (2.2 eq.) and NEt3 (2.5 eq.) in CH2Cl2 (0.2 ml/mmol) was added dropwise. After stirring 6 hours at room temperature, the mixture was diluted with EtOAc and washed with 1 M HCl, 1 M NaHCO3, brine, dried with Na2SO4 and the solvent evaporated. The residue was purified via flash chromatography (CH2Cl2) affording a colorless oil (88% yield).

Figure 10:
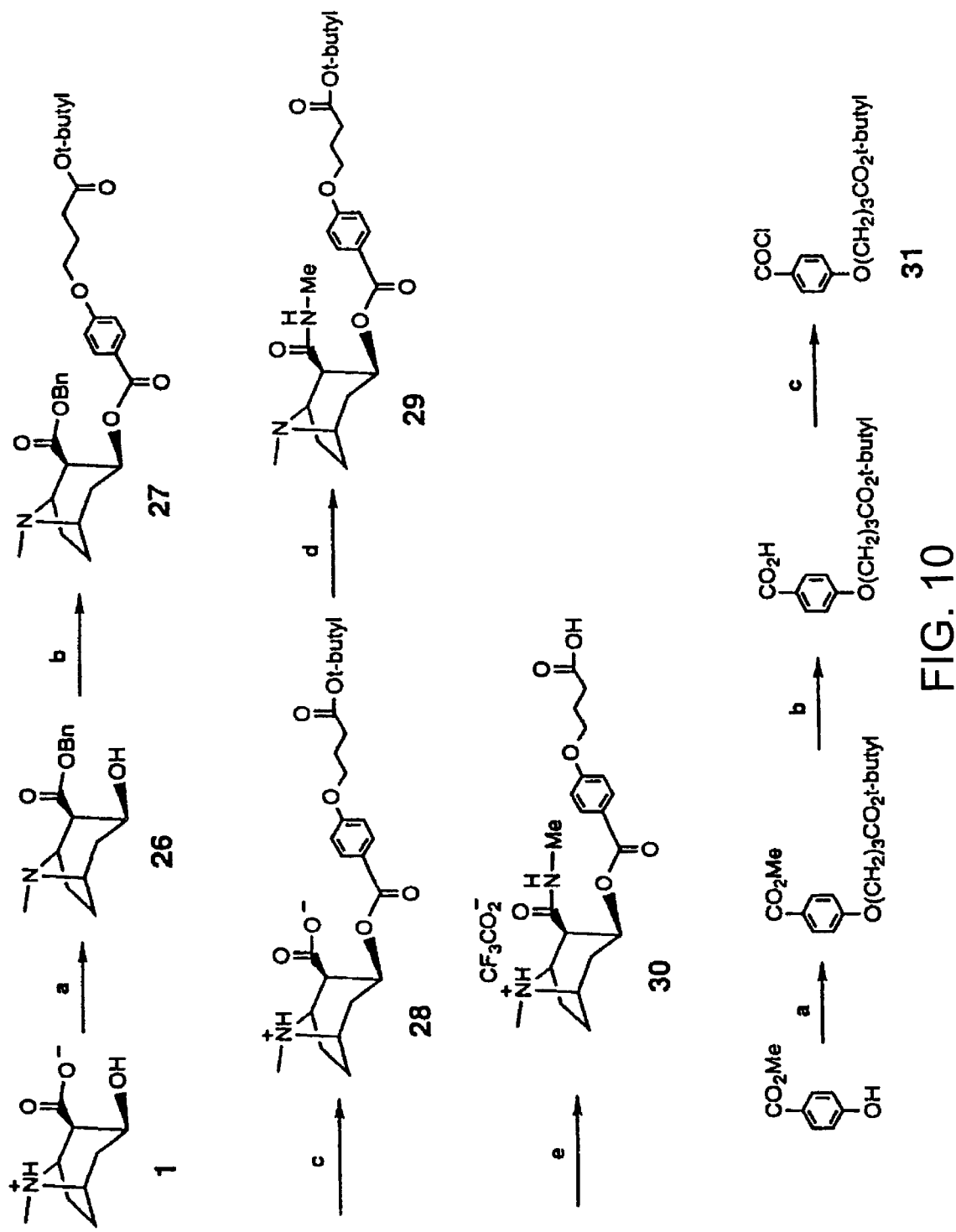
FIG. 10 illustrates the synthesis of hapten 30 using the following steps; top scheme: a) (i) benzyl bromide, $Me_4NOH$, MeOH, DMF, (ii) free-base; b) add 31, $NEt_3$; c) $H_2$, Pd/C; d) methylamine, EDC, DMF; e) trifluoroacetic acid; lower scheme illustrates the synthesis of compound 31 using the following steps: a) $Br(CH_2)_5CO_2$t-butyl, NaH; b) dilute NaOH; c) oxalyl chloride.

Synthesis of Compound 26 (FIG. 10, Step a)

Compound 26. Compound 1 (2.0 g, 9.0 mmol) was suspended in a mixture of pyridine (250 ml, 3.1 mmol), finely powdered NaOH (760 mg, 19 mmol) and benzylbromide (7.8 g, 27 mmol). The mixture was heated to 80° C. and allowed to stir for 20 hours. After cooling to room temperature, the mixture was diluted with 1.25 M HCl (60 ml) and washed with several portions of ether. The ether layer was back-extracted with several portions of 1.25 M HCl. The combined aqueous layers were cooled in an ice bath and diluted with CHCl3 (30 ml). The mixture was stirred and solid K2CO3 was added carefully until pH 9. The phases were separated and the aqueous layer extracted with CHCl3 (3×30 ml) and the combined extracts washed with brine and dried with Na2SO4. The solvent was evaporated leaving a dark brown oil that was triturated with EtOAc. The liquid layer was decanted away from the undesired solid residue. The residue was washed with several portions of EtOAc. The combined EtOAc (150 ml) was dried with Na2SO4 and the solvent evaporated leaving a homogeneous, brown oil (3.8 g). This was purified via flash chromatography (90/10/1 CH2Cl2/MeOH/NH4OH) affording a translucent, light-brown oil (crystallized upon long standing) (2.1 g, 60%). The benzyl 6-bromohexanoate used above was synthesized from 6-bromohexanoic acid (1.0 eq.) (Aldrich Chemical Co.), benzyl alcohol (1.3 eq.), and p-toluenesulphonic acid (0.05 eq.) in refluxing cyclohexane (1.5 ml/mmol 6 -Br-hexanoic acid) with the aid of a Dean-Stark trap. After 2 hours, the solution was allowed to cool to room temperature and the solvent removed on a rotary evaporator. The residue was diluted with EtOAc, washed with 1 M NaHCO3, brine, dried with MgSO4 and the solvent evaporated. The residue was distilled (benzyl alcohol forerun) affording a clear, colorless liquid (87% yield) (bp 150–155° C., 4 mmHg).

Synthesis of Compound 27 (FIG. 10, Step b)

Compound 27. Compound 26 (250 mg, 0.64 mmol) was dissolved in CH2Cl2 (1.5 ml). The solution was cooled in an ice bath and then NEt3 (107 ul, 0.77 mmol), compound 31 (1.1 equivalents; vida infra) and DMAP (4-dimethylaminopyridine) (10 mg, 0.077 mmol) were added. The mixture was allowed to stir at room temperature for 6 hours or until complete, as monitored by TLC. The mixture was diluted with EtOAc and washed with 3.5 M K2CO3, brine, dried with Na2SO4 and the solvent evaporated. The residue was purified via flash chromatography (95/5/1 CH2Cl2/MeOH/NH4OH) affording a thick, straw-colored oil (190 mg, 60%).

Synthesis of Compound 28 (FIG. 10, Step c)

Compound 28. To a solution of compound 27 (136 mg, 0.275 mmol) in MeOH (3 ml) was added 10% Pd/C (30 mg). The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%).

Synthesis of Compound 29 (FIG. 10, Step d)

Compound 29. The compound 28 (1.0 eq.), methylamine hydrochloride (1.2 eq.) and NEt3 (2.2 eq.) are dissolved in DMF (0.5 M solution), and then 1-(3-dimethylaminopropyl)-3-ethyl-carbodiimide hydrochloride (EDC) (1.3 eq.) and DMAP (0.013 eq.) is added at 0° C. The reaction mixture is stirred for 24 hours at room temperature. The mixture is diluted with EtOAc and the organic layer washed with saturated 1 M HCl, 1 M NaHCO3, and brine. After drying over Na2SO4 and removal of the solvent, the residue is purified via flash chromatography.

Synthesis of Compound 30 (FIG. 10, Step e)

Compound 30. The compound 29 is dissolved in CH2Cl2 (1.0 M solution) and cooled in an ice bath. Trifluoroacetic acid (3.0 eq.) is added and the solution stirred for 1 hour at room temperature. The solvent and volatiles are then thoroughly evaporated. The compound is obtained as a salt and does not require further purification.

Synthesis of Compound 31 (FIG. 10, Steps a–c)

Compound 31. Step a: Methyl-p-hydroxybenzoate (1.0 eq. (Aldrich) is dissolved in DMF (1.0 M solution) and added dropwise to a stirring, ice-cold suspension of oil-free NaH (1.1 eq.) in DMF (0.5 M suspension). After 15 minutes, benzyl 4-bromobutanoate (1.1 eq.) (see compound 13) is added followed by tetrabutylammoniumiodide (0.011 eq.). The ice bath is removed and the mixture stirred for 2 hours at room temperature. EtOAc is added and the mixture washed thoroughly with brine, dried with Na2SO4, and solvent evaporated. The residue is purified via flash chromatography. Step b: The compound from step a is dissolved in MeOH (0.5 M solution) and cooled in an ice bath. A solution of LiOH (20 eq.) in water (0.5 M solution) is then added. After 3 hours, the mixture is acidified, the compound extracted with EtOAc and the organic layer washed with brine and dried. Step c: The compound from step b is dissolved in THF (1.0 M solution) containing a drop of DMF and the solution cooled in an ice bath. Oxalyl chloride (1.1 eq.) is added and the solution stirred for 1 hour at room temperature. The solvent and volatiles are then thoroughly evaporated and the compound used without further purification. The t-butyl 4-bromobutanoate used in step a is synthesized from 4-bromobutanoic acid (1.0 eq.) (Aldrich) suspended in hexane containing a catalytic amount of Amberlyst-H+ resin and excess isobutylene. The mixture is stirred for 16 hours at room temperature. After filtration and evaporation of the solvent, the compound is used without further purification.

Figure 11:
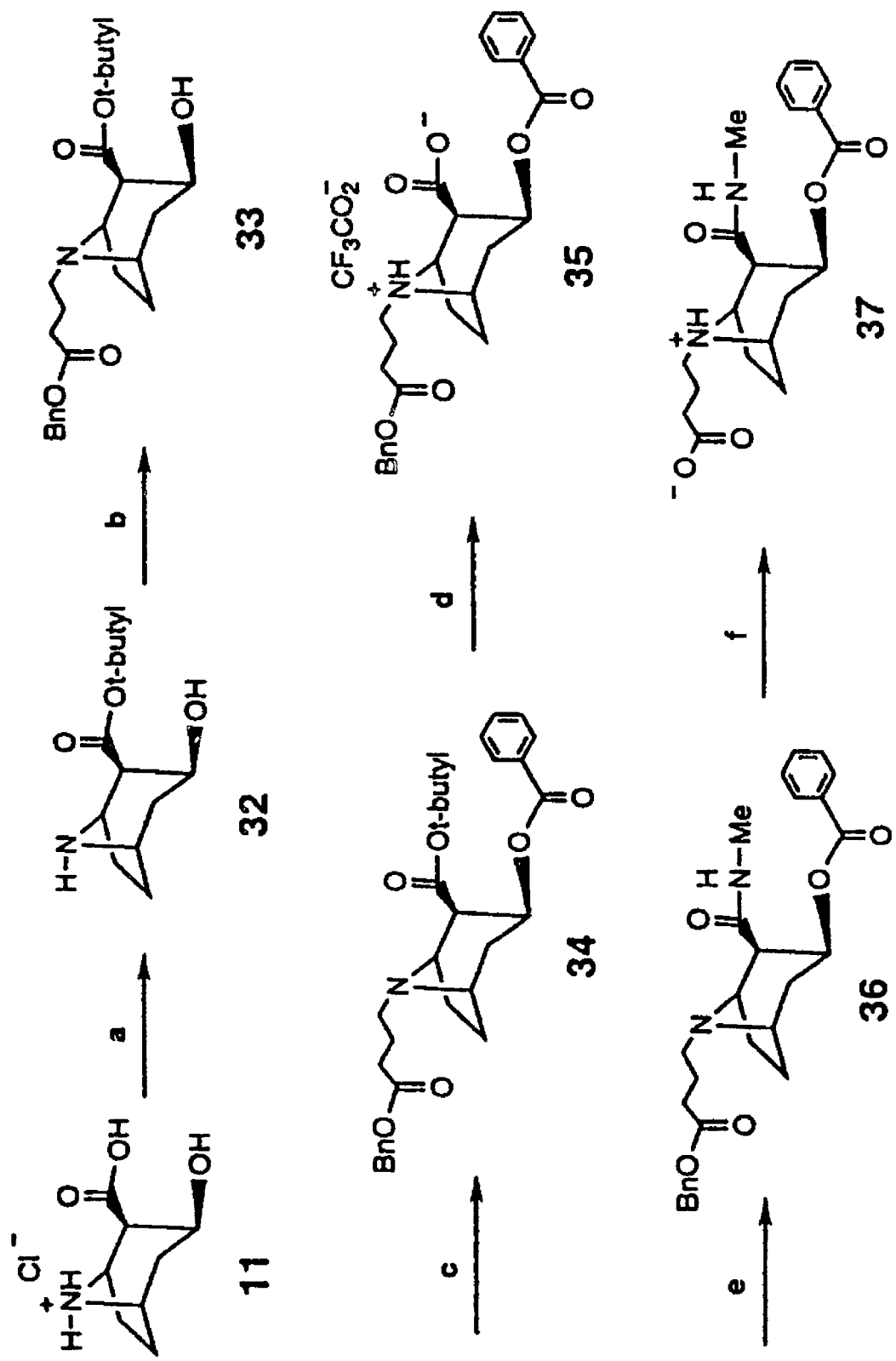
FIG. 11 illustrates the synthesis of hapten 37 using the following steps: a) (i) isobutylene, $H_2SO_4$, (ii) free base; b) $Br(CH_2)_5CO_2Bn$, $NEt_3$; c) benzoyl chloride, $NEt_3$, DMAP; d) trifluoroacetic acid; e) methylamine, EDC; f) $H_2$, Pd/C.

Synthesis of Compound 32 (FIG. 11, Step a)

Compound 32. The compound 11 (1.0 eq.) is suspended in CH2Cl2 containing a catalytic amount of sulfuric acid and excess isobutylene. The mixture is stirred for 16 hours at room temperature. After evaporation of the solvent, the residue is partitioned between chloroform and K2CO3 solution. The organic layer is dried and evaporated to afford the compound as the free base that is used without further purification.

Synthesis of Compound 33 (FIG. 11, Step b)

Compound 33. Compound 32 (1.0 eq.) was dissolved in CH3CN (4 ml/mmol 12). NEt3 (1.2 eq.), benzyl 4-bromobutanoate (1.2 eq.) (prepared in a similar fashion to the hexanoate, see compound 2) and tetrabutyl-ammoniumiodide (0.1 eq.) were then added. The mixture was heated at 50° C. for 24 hours. After dilution with EtOAc and the usual workup (see compound 3), the crude residue was purified via flash chromatography (95/5/1 EtOAc/MeOH/NH4OH) affording a clear, straw-colored oil (58% yield).

Synthesis of Compound 34 (FIG. 11, Step c)

Compound 34. Compound 33 (250 mg, 0.64 mmol) was dissolved in CH2Cl2 (1.5 ml). The solution was cooled in an ice bath and then NEt3 (107 ul, 0.77 mmol) and DMAP (4-dimethylamino-pyridine) (10 mg, 0.077 mmol) were added. The mixture was allowed to stir at room temperature for 6 hours or until complete, as monitored by TLC. The mixture was diluted with EtOAc and washed with 3.5 M K2CO3, brine, dried with Na2SO4 and the solvent evaporated. The residue was purified via flash chromatography (95/5/1 CH2Cl2/MeOH/NH4OH) affording a thick, straw-colored oil (190 mg, 60%).

Synthesis of Compound 35 (FIG. 11, Step d)

Compound 35. The compound 34 is dissolved in CH2Cl2 (1.0 M solution) and cooled in an ice bath. Trifluoroacetic acid (3.0 eq.) is added and the solution stirred for 1 hour at room temperature. The solvent and volatiles are then thoroughly evaporated. The compound is obtained as a salt and does not require further purification.

Synthesis of Compound 36 (FIG. 11, Step e)

Compound 36. The compound 35 (1.0 eq.), methylamine hydrochloride (1.2 eq.) and NEt3 (2.2 eq.) are dissolved in DMF (0.5 M solution), and then 1-(3-dimethylaminopropyl)-3-ethyl-carbodiimide hydrochloride (EDC) (1.3 eq.) and DMAP (0.013 eq.) is added at 0° C. The reaction mixture is stirred for 24 hours at room temperature. The mixture is diluted with EtOAc and the organic layer washed with saturated 1 M HCl, 1 M NaHCO3, and brine. After drying over Na2SO4 and removal of the solvent, the residue is purified via flash chromatography.

Synthesis of Compound 37 (FIG. 11, Step f)

Compound 37. To a solution of compound 35 (136 mg, 0.275 mmol) in MeOH (3 ml) was added 10% Pd/C (30 mg). The reaction mixture was shaken on a Parr apparatus under 40 psi of hydrogen for 6 hours. After this time, the mixture was filtered through a pad of celite in a sintered glass funnel washing with MeOH. The solvent was removed on a rotary evaporator and the residue thoroughly dried under vacuum affording a colorless, hygroscopic solid that required no further purification (110 mg, 99%).

Figure 12:
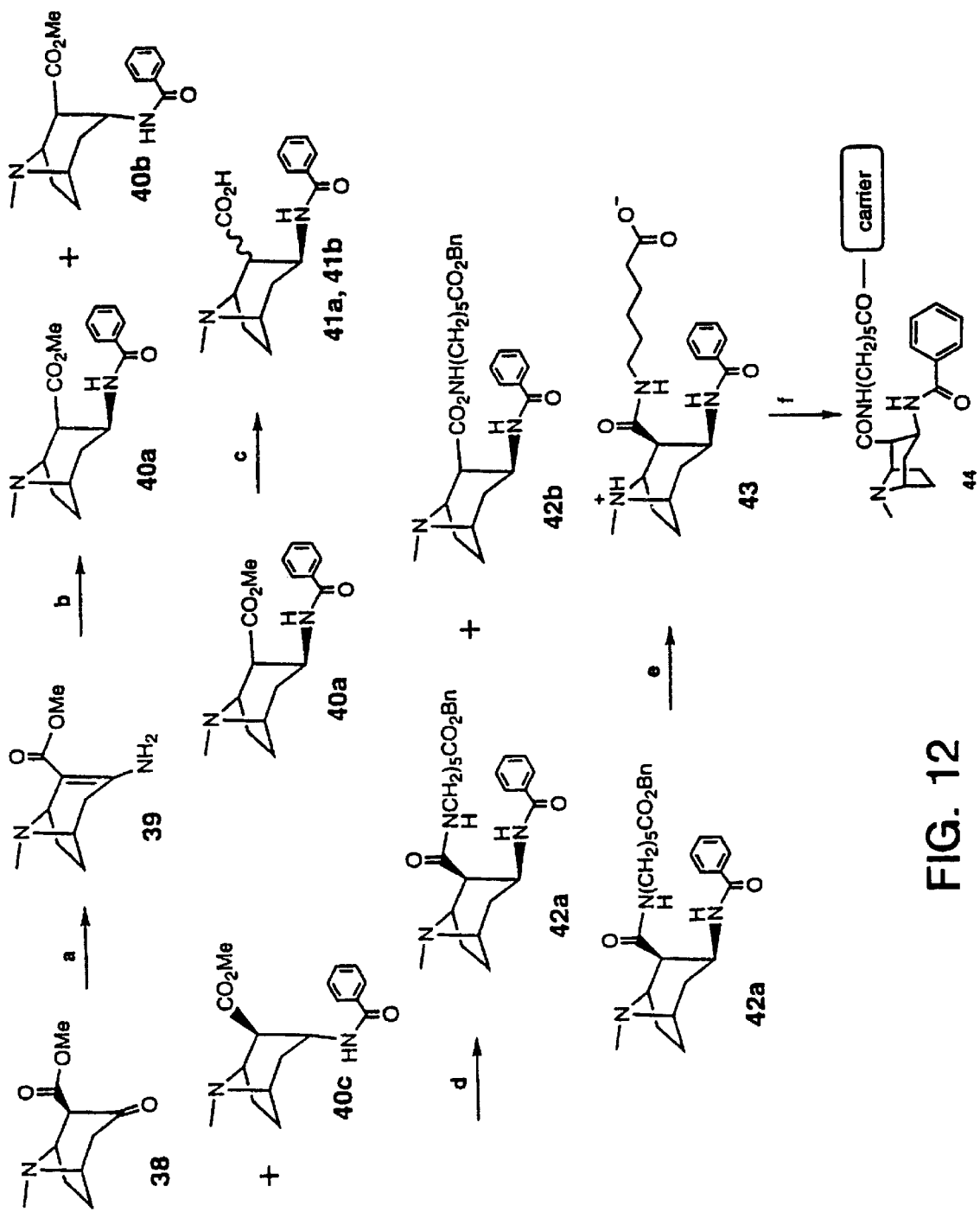
FIG. 12 illustrates the synthesis of hapten 43 using the following steps: a) $NH_4OAc$, HOAc, benzene, reflux; b) (i) $NaCNBH_3$, pH 4, MeOH, RT, (ii) benzoyl chloride, $NaHCO_3$, dioxane-$H_2O$, (iii) separation of isomers; c) $H_2O$, reflux; d) (i) $H_2N(CH_2)_5CO_2Bn$ tosylate, EDC, $NEt_3$, DMAP, (ii) separation of isomers; e) $H_2$, Pd/C, MeOH; f) (i) Sufosuccinimide, EDC-HCl, r.t. (ii) KLH or BSA, r.t.
Figure 13:
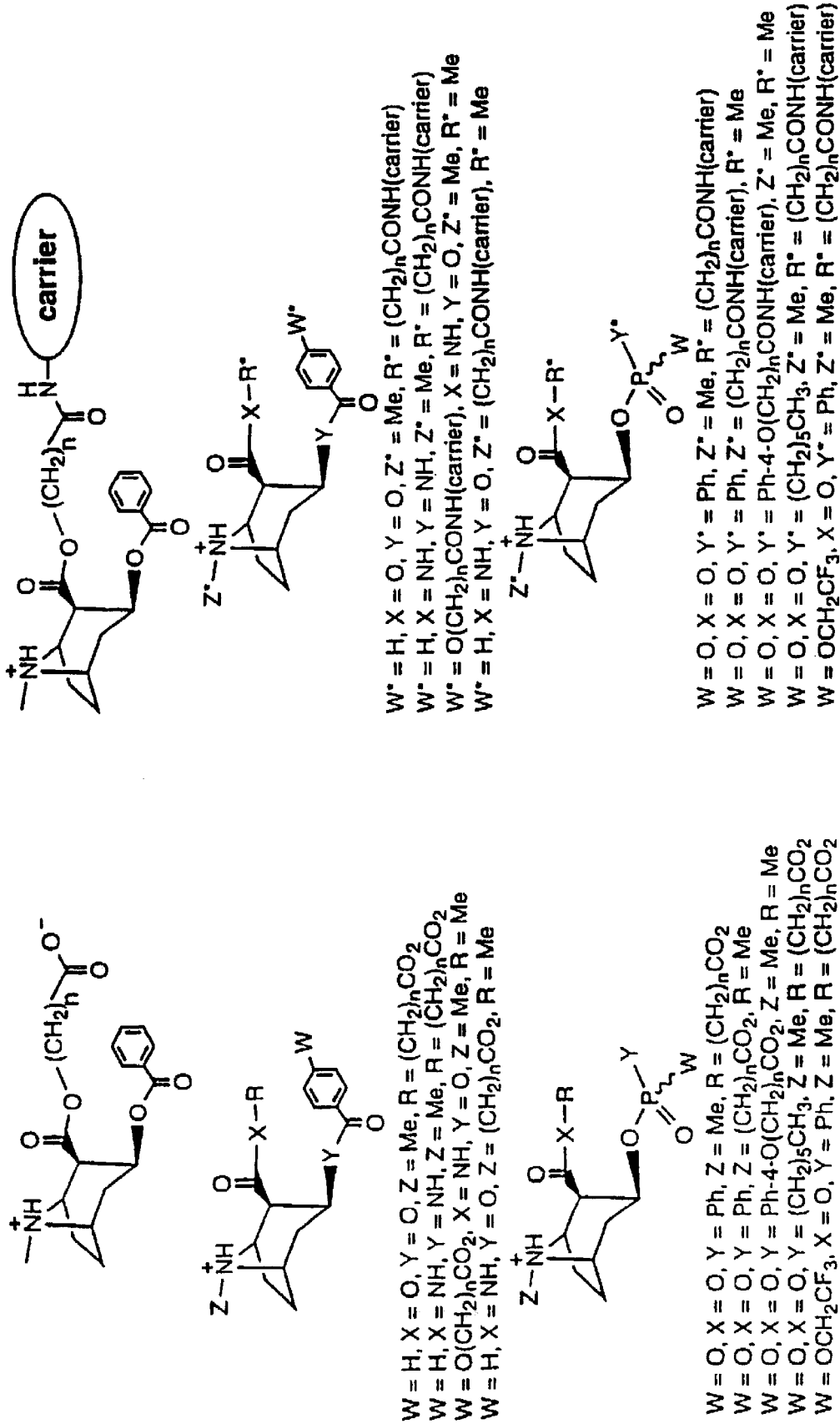
FIG. 13 illustrates the general structures of haptens (left column) and conjugates (right column).

Synthesis of Compound 39, (1R)-3-amino-8-methyl-8-azabicyclo[3.2.1]oct-2-ene-2-carboxylic acid methyl ester (FIG. 12; Step a)

Compound 39. Ammonium acetate (391 mg, 5.07 mmol) was added to a solution of (1R)-(+)-2-carbomethoxy-3-tropinone 38 (200 mg, 1.01 mmol) (S. P. Findlay, J. Org. Chem. (1957): vol: 22, p 1385–1394; F. I. Carroll, et al., J. Org. Chem. (1982): vol. 47, p 13–19; A. H. Lewin, et al., J. Heterocyclic Chem. (1987): vol. 24, p 19–21; P. C. Meltzer, et al., J. Med. Chem. (1994): vol. 37, p 2001–2010) in benzene/acetic acid (17.5 ml/0.1 ml). The mixture was refluxed for 10 hours. To this reaction mixture was added CH2Cl2 and c-NH4OH. The organic layer was collected and dried over Na2SO4. After removal of the solvent, the residue was purified via flash chromatography (CH2Cl2/MeOH/c-NH4OH; 20/1/0.02 to 5/1/0.02) affording colorless crystals (160 mg, 80%). 1H NMR (300 MHz, CDCl3): d 1.42–1.53 (1H, m), 1.68– 1.81 (3H, m), 2.01–2.19 (3H, m), 2.31 (3H, s), 2.73 (1H, dd, J=4.9, 17.1 Hz), 3.36 (1H, t, J=5.7 Hz), 3.67 (3H, 5), 3.82 (1H, d, J=5.1 Hz). 13C NMR (75 MHz, CDCl3): d 29.0, 33.9, 34.9, 36.6, 50.4, 57.4, 57.9, 150.5, 153.8, 169.2. mp 95–98° C. HRMS (FAB) m/e calcd for C10H16N2O2+H+, 197.1290; found 197.1287.

Synthesis of Compound 40a, [1R-(2-endo,3-exo)]-3-(benzoylamino)-8-methyl-8-azabicyclo[3.2.1]-octane-2-carboxylic acid methyl ester; compound 40b, [1R-(endo,endo)]-3-(benzoylamino)-8-methyl-8-azabicyclo[3.2.1]octane-2-carboxylic acid methyl ester; Compound 40c, [1R-(2-exo,3-endo)]-3-(benzoylamino)-8-methyl-8-azabicyclo[3.2.1]octane-2-carboxylic acid methyl ester (FIG. 12; Step b)

Compounds 40a, 40b, 40c. Compound 39 (667 mg, 3.40 mmol) was dissolved in MeOH (6 ml), then 2 M HCl in dioxane/MeOH was added and the pH adjusted to pH 4. Sodium cyanoborohydride (214 mg, 3.40 mmol) was added and the mixture stirred for 18 hours at room temperature. The solvent was removed in vacuo and the residue was dissolved in dioxane/H2O (2 ml/2 ml). To this solution was added NaHCO3 (1.43 g, 17.0 mmol) and benzoyl chloride (0.79 ml, 6.80 mmol), and the mixture stirred for 20 hours. The mixture was diluted with CH2Cl2 and c-NH4OH and the organic layer collected and dried over Na2SO4. After removal of the solvent, the residue was purified via flash chromatography (CH2Cl2/MeOH/c-NH4OH; 20/1/0.02 to 5/1/0.02) affording, in order of polarity: 40a (195 mg, 19%), 40b (196 mg, 19%) and 40c (62 mg, 6%) as oils. Compound 40a: 1H NMR (300 MHz, CD3OD): d 1.58–2.31 (8H, m), 2.45 (3H, s), 3.06 (1H, dd, J=2.7, 11.5 Hz), 3.28–3.32 (1H, m), 3.45–3.50 (1H, m), 3.67 (3H, s), 4.58 (1H, dt, J=6.2, 11.4 Hz), 7.48– 7.60 (3H, m), 7.78–7.84 (2H, m). 13C NMR (75 MHz, CDCl3): d 23.6, 26.2, 35.6, 38.5, 43.2, 49.6, 51.9, 60.4, 62.8, 126.9, 128.4, 131.3, 134.5, 166.8, 172.5. HRMS (FAB) m/e calcd for C17H22N2O3+H+, 303.1709; found 303.1724. Compound 40b: 1H NMR (300 MHz, CD3OD): d 1.92–2.43 (11H, m) including 2.40 (3H, s), 3.24–3.31 (2H, m), 3.41–3.48 (1H, m), 3.66 (3H, s), 4.61 (1H, t, J=6.2 Hz), 7.42–7.62 (3H, m), 7.73–7.78 (2H, m). 13C NMR (75 MHz, CDCl3): d 23.8, 25.2, 36.0, 39.9, 43.3, 47.3, 51.8, 59.9, 61.7, 126.7, 128.7, 131.5, 134.6, 166.7, 173.4. HRMS (FAB) m/e calcd for C17H22N2O3+H+, 303.1709; found 303.1720. Compound 40c: 1H NMR (300 MHz, CD3OD): d 1.80–1.89 (1H, m), 1.95–2.40 (8H, m) including 2.35 (3H, s), 2.93–2.98 (1H, m), 2.95–2.99 (1H, m), 3.20–3.28 (1H, m), 3.66–3.71 (1H, m) 3.78 (3H, s), 4.55 (1H, dt, J 2.2, 7.2 Hz), 7.48–7.62 (3H, m), 7.75–7.82 (2H, m). 13C NMR (75 MHz, CDCl3): d 24.5, 25.6, 36.2, 41.6, 42.7, 51.7, 52.1, 60.9, 63.2, 126.6, 128.7, 131.5, 134.5, 166.3, 172.8. HRMS (FAB) m/e calcd for C17H22N2O3+H+, 3.03.1709; found 303.1704.

Synthesis of Compound 41a, [1R-(exo,exo)]-3-(benzoylamino)-8-methyl-8-azabicyclo[3.2.1]octane-2-carboxylic acid; Compound 41b, [1R-(2-endo,3-exo)]-3-(benzoylamino)-8-methyl-8-azabicyclo-[3.2.1]octane-2-carboxylic acid (FIG. 12; Step c)

Compounds 41a, 41b. Compound 40a (138 mg, 0.456 mmol) was dissolved in water (10 ml) and the solution refluxed for 24 hours. The solution was lyophilized affording a 50/50 mixture of diastereomers as a fluffy powder (123 mg, 93%). 1H NMR (300 MHz, CD3OD): d 1.98–2.52 (6H, m), 2.45 and 2.88 (3H, each s), 2.94 (0.4H, dd, J 2.7, 6.5 Hz), 3.18 (0.6H, dd, J=2.5, 11.5 Hz), 3.88–3.95 (1H, m), 4.05–4.10 (1H, m), 4.42–4.62 (1H, m), 7.47–7.60 (3H, m), 7.79–7.88 (2H, m). 13C NMR (125 MHz, D2O): d 20.5, 22.5, 23.0, 30.2, 31.9, 34.1, 37.3, 37.8, 39.9, 41.9, 48.2, 51.6, 62.0, 63.1, 64.4, 65.0, 126.5, 128.1, 131.5, 131.6, 132.8, 132.9, 169.9, 170.0, 174.2, 176.8. HRMS (FAB) m/e calcd for C16H20N2O3+Na+, 311.1372; found 311.1382.

Synthesis of Compound 42a, [1R-(exo,exo)]-6-[[[3-(benzoylamino)-8-methyl-8-azabicyclo[3.2.1]oct-2-yl]carbonyl]amino]-hexanoic acid phenylmethyl ester; Compound 42b, [1R-(2-endo,3-exo)]-6-[[[3-(benzoylamino)-8-methyl-8-azabicyclo[3.2.1]oct-2-yl]carbonyl]-amino]-hexanoic acid phenylmethyl ester (FIG. 12; Step d)

Compounds 42a, 42b. The mixture of 41a and 41b (39 mg, 0.14 mmol), 6-aminohexanoic acid benzyl ester tosylate (64 mg, 0.16 mmol) and NEt3 (23 ml, 0.16 mmol) were dissolved in CH2Cl2 (0.7 ml) and then EDC (33.6 mg, 0.18 mmol) and DMAP (1.6 mg, 0.014 mmol) were added at 0° C. The reaction mixture was stirred for 24 hours at room temperature. The mixture was diluted with CH2Cl2 and the organic layer washed with saturated NaHCO3 and water. After drying over Na2SO4 and removal of the solvent, the residue was purified by preparative TLC (CH2Cl2/MeOH/c-NH4OH; 5/1/0.02) affording 42a (12 mg, 18%) and 42b (27 mg, 41%) as oils. Compound 42a: 1H NMR (300 MHz, CD3OD): d 1.34–2.45 (17H, m) including 2.32 (3H, s), 2.78 (1H, dd, J=2.7, 6.4 Hz), 3.17–3.35 (3H, m), 3.41–3.48 (1H, m), 4.45 (1H, dt, J=6.3, 12.5 Hz), 5.12 (2H, s), 7.35–7.51 (8H, m), 7.75–7.82 (2H, m). 13C NMR (125 MHz, CDCl3): d 24.5, 24.7, 25.6, 26.6,. 29.3, 34.1, 36.3, 38.8, 40.6, 41.5, 49.7, 60.9, 63.2, 66.1, 127.0, 128.2 (overlapping, 128.22), 128.5, 128.6, 131.3, 134.2, 136.0, 166.7, 172.9, 173.3. HRMS (FAB) m/e calcd for C29H37N3O4+H+, 492.2862; found 492.2873. Compound 42b: 1H NMR (300 MHz, CD3OD): d 1.18–1.58 (6H, m), 2.08–2.68 (8H, m), 2.81 (3H, s), 3.02–3.26 (2H, m), 3.28 (1H, dt, J=2.5, 11.3 Hz), 3.85–3.95 (2H, m), 4.62–4.74 (1H, m), 5.12 (2H, s), 7.35–7.55 (8H, m), 7.81–7.90 (2H, m). 13C NMR (125 MHz, CDCl3): d 23.5, 24.4, 26.1, 26.3, 28.9, 33.9, 36.6, 38.6, 39.3, 42.0, 52.6, 60.8, 64.1, 66.0, 126.9, 128.1, 128.4, 128.5, 131.8, 133.4, 135.9, 167.6, 170.8, 173.2. HRMS (FAB) m/e calcd for C29H37N3O4+Cs+, 624.1838; found 624.1820.

Synthesis of Compound 43, [1R-(exo,exo)]-6-[[[3-(benzoylamino)-8-methyl-8-azabicyclo[3.2.1]oct-2-yl]carbonyl]amino]-hexanoic acid (FIG. 12; Step e)

Compound 43. Compound 42a (17 mg, 0.0346 mmol) was dissolved in MeOH (1 ml) and then 10% Pd/C (20 mg) was added. The reaction mixture was stirred for 1 hour under H2 (1 atm) at room temperature then filtered and concentrated. The residue was dissolved in water and lyophilized affording a fluffy powder (13 mg, 94%). 1H NMR (300 MHz, CD3OD): d 1.20–1.58 (6H, m), 2.03–2.27 (5H, m), 2.38–2.67 (m, 3H), 2.80 (3H, s), 3.13 (1H, dd, J=2.6, 6.3 Hz), 3.15–3.33 (2H, m), 3.92–3.97 (1H, m), 4.05–4.10 (1H, m), 4.60 (1H, dt, J=6.4, 12.8 Hz), 7.48–7.61 (3H, m), 7.81–7.90 (2H, m). 13C NMR (75 MHz, D2O): d 22.0, 22.9, 24.5, 25.2, 27.4, 31.7, 36.4, 37.7, 38.5, 40.7, 45.4, 62.4, 64.0, 126.5, 128.1, 131.9, 132.1, 170.3, 171.9, 182.9. [a]/O(D, 25)=−75.60 (c=0.5, methanol). HRMS (FAB) m/e calcd for C22H31N3O4+Na+, 402.2393; found 402.2405.

Synthesis of Compound 44 (Scheme 8)

Compound 44. Compound 43 was suspended in 0.10 Molar DMF at 0° C. Next, 1.1 equivalents sufosuccinimide (Aldrich) and 1.1 equivalents EDC (1-3-Dimethylaminopropyl)-3-ethyl-carbo-diimide-hydrochloride Aldrich) were added and the mixture was stirred for 2 hours at 25° C. Next, either 1.1 equivalents KLH (keyhole limpet hemacyanin; Sigma) or 1.1 equivalents BSA (bovine serum albumin; Sigma) was added and the mixture was stirred at 25° C. for 12 hours. The mixture was next quenched with successive saturated solution washes of ammonium chloride, water and dried over magnesium sulfate. The compound was purified via reverse phase HPLC to afford compound 44.

What is claimed is:

1. A compound having a formula selected from the group consisting of:

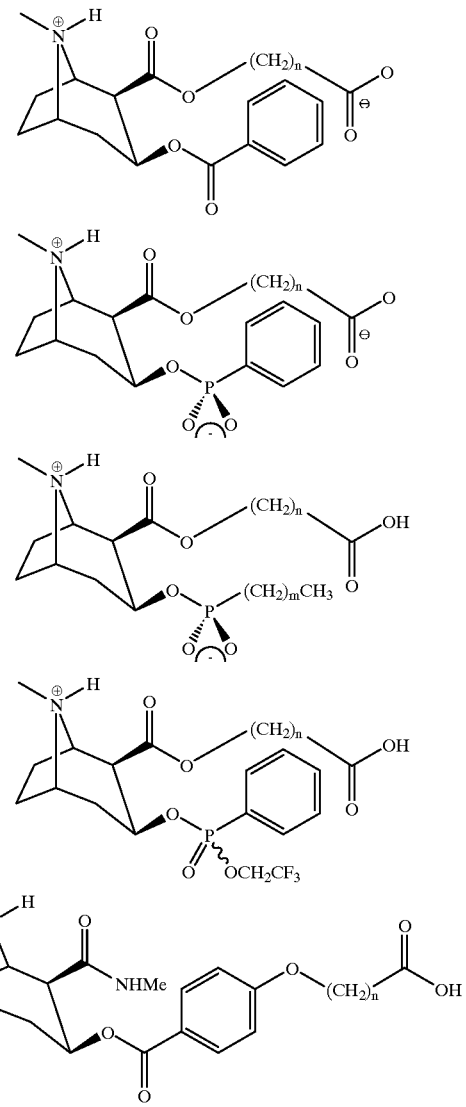

-continued

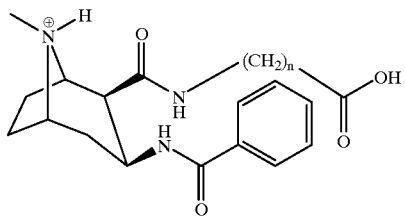

wherein n and m are integers from 2 to 8.

2. The compound of claim 1, wherein said compound has the following formula:

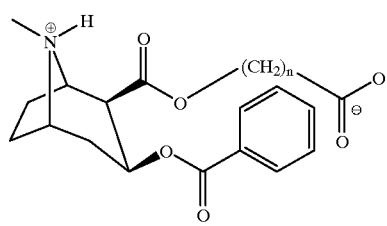

wherein n is an integer from 2 to 8.

3. The compound of claim 2, wherein n is an integer from 4 to 6.

4. The compound of claim 3, wherein n is 5.

5. A compound having a formula selected from the group consisting of:

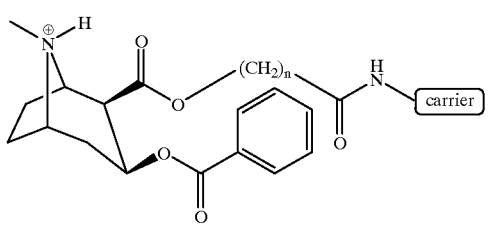

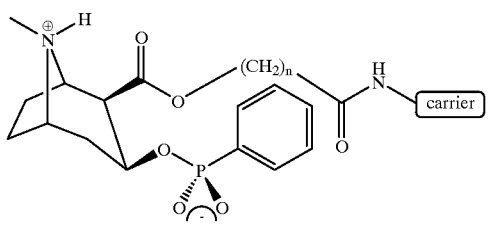

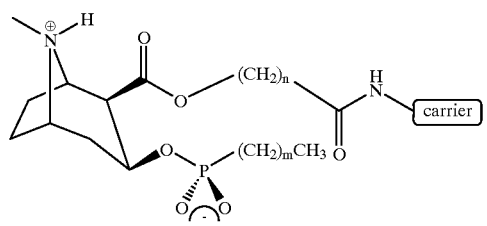

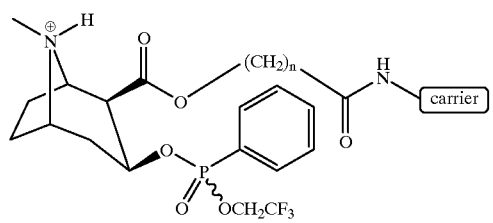

-continued

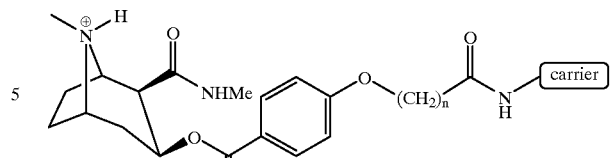

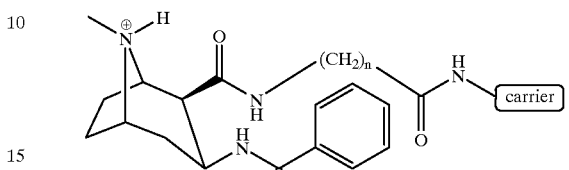

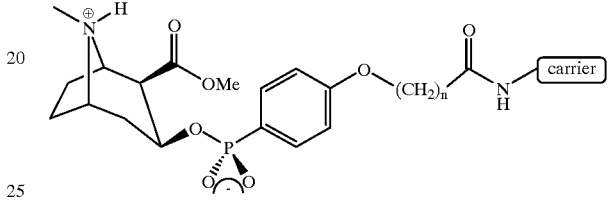

wherein n and m are integers from 2 to 8.

6. The compound of claim 5, wherein said compound has the following formula:

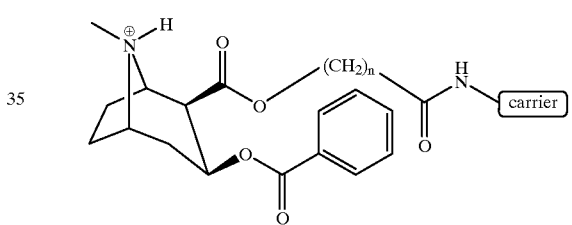

wherein n is an integer from 2 to 8.

7. The compound of claim 6, wherein n is an integer from 4 to 6.

8. The compound of claim 7, wherein is 5.

9. Antisera resulting from immunization with a compound having a formula selected from the group consisting of:

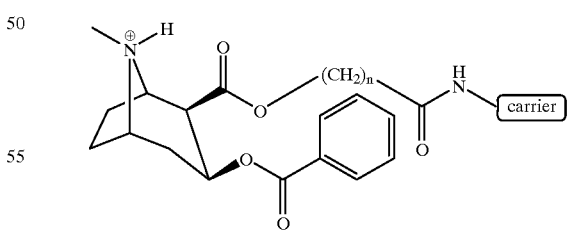

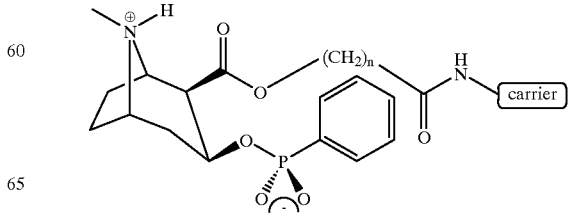

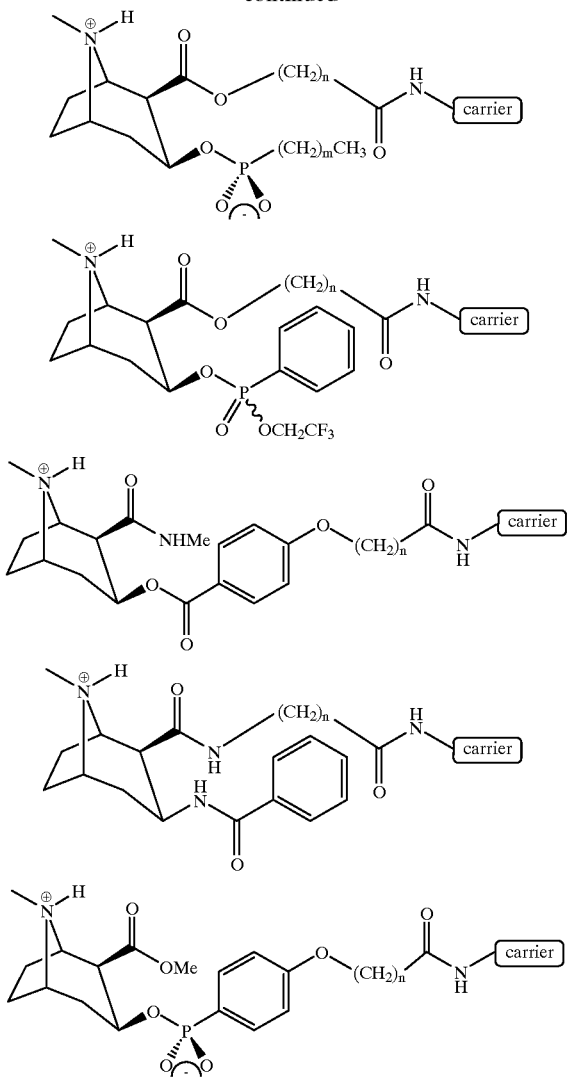

wherein n and m integers from 2 to 8.

10. The antisera of claim 9, wherein said compound has the following formula:

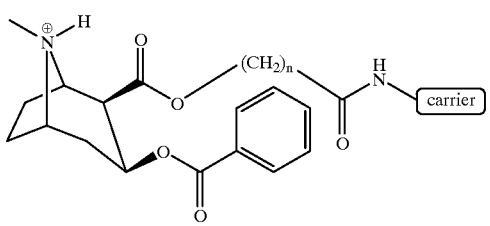

wherein n is an integer from 2 to 8.

11. The antisera of claim 10, wherein in said compound n is an integer from 4 to 6.

12. The antisera of claim 11, wherein in said compound n is 5.

13. A monoclonal antibody resulting from immunization with a compound having a formula selected from the group consisting of:

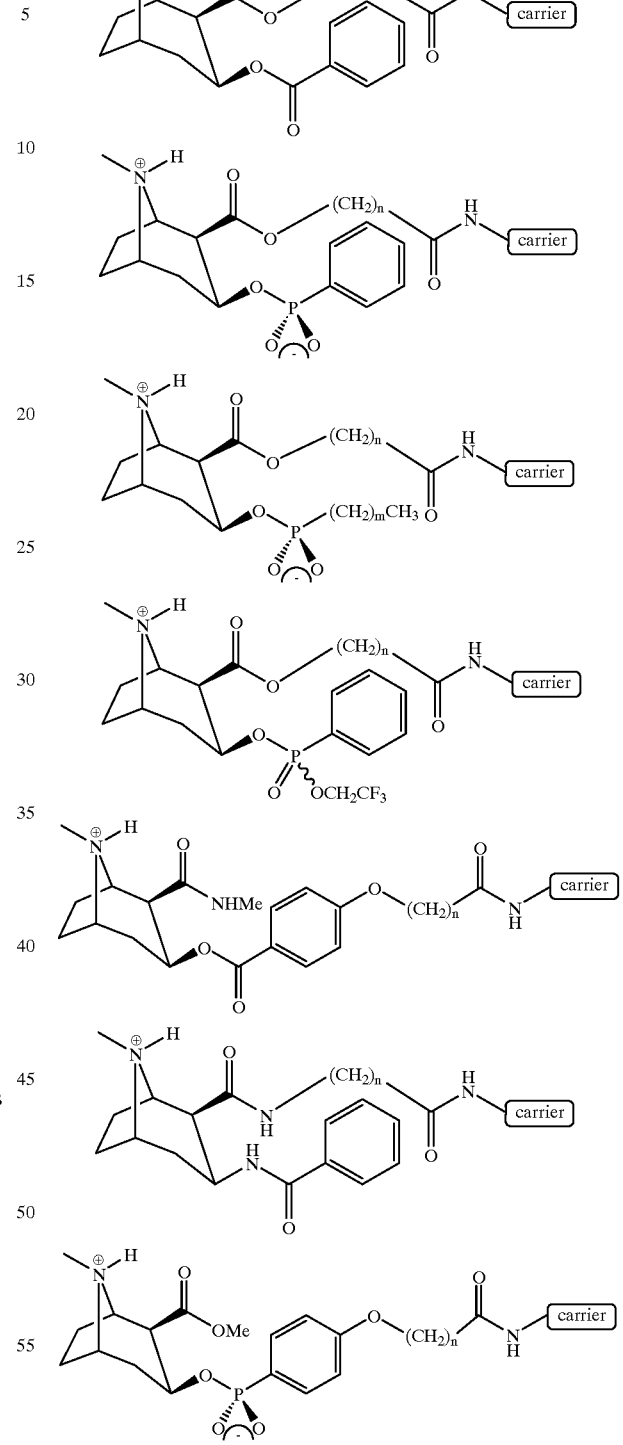

wherein n and m are integers from 2 to 8, isolation of an anti-cocaine antibody producing cell which expresses said monoclonal antibody, cloning of said cell, and isolation of said monoclonal antibody expressed by said cloned cell.

14. The monoclonal antibody of claim 13, wherein said compound has the following formula:

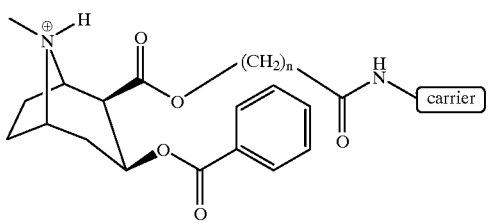

wherein n is an integer from 2 to 8.

15. The monoclonal antibody of claim 14, wherein in said compound n is an integer from 4 to 6.

16. The monoclonal antibody of claim 15, wherein in said compound n is 5.

17. A method of producing antisera specific for cocaine, said method comprising:

immunizing a subject with a compound having a formula selected from the group consisting of:

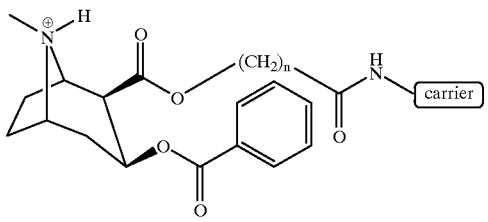

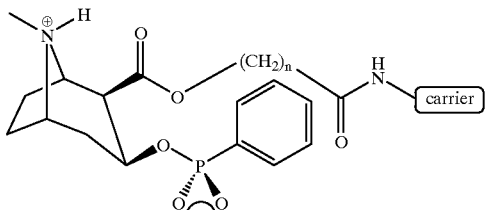

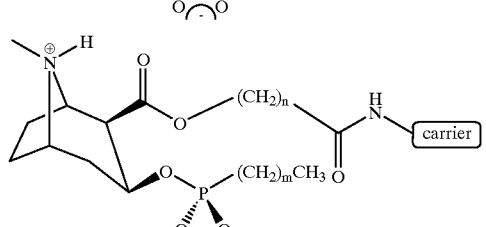

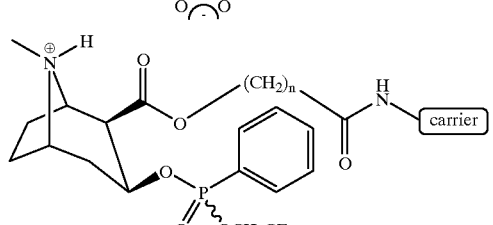

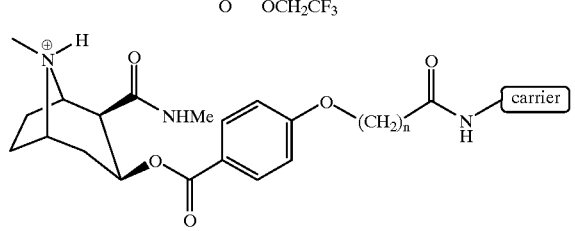

-continued

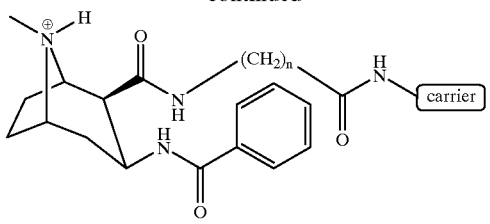

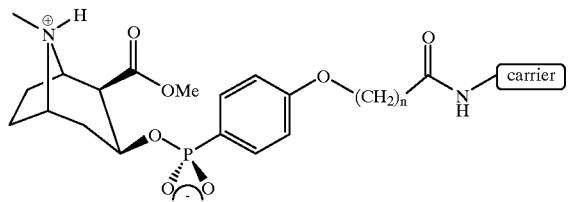

wherein n and m are integers from 2 to 8; and isolating antisera from said subject.

18. The method of claim 17, wherein said compound has the following formula:

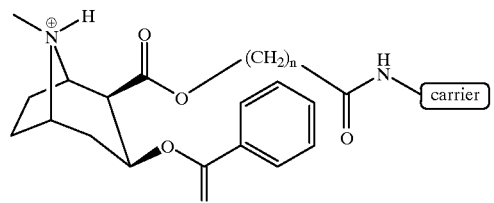

wherein n is an integer from 2 to 8.

19. The method of claim 18, wherein in said compound n is an integer from 4 to 6.

20. The method of claim 19, wherein in said compound n is 5.

21. A method of producing a monoclonal antibody specific for cocaine, said method comprising:

immunizing a subject with a compound having a formula selected from the group consisting of:

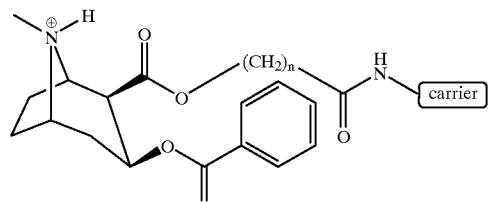

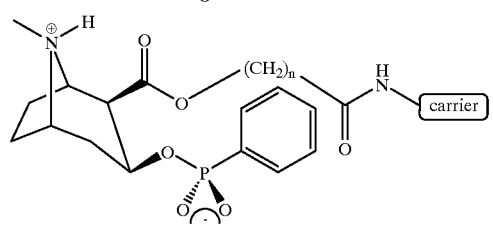

-continued

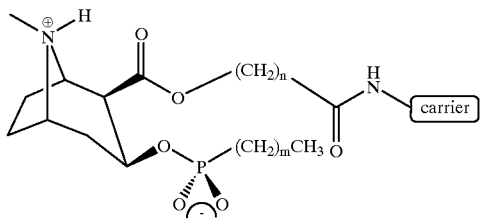

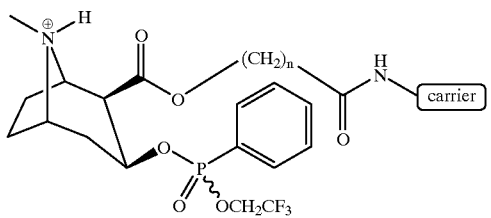

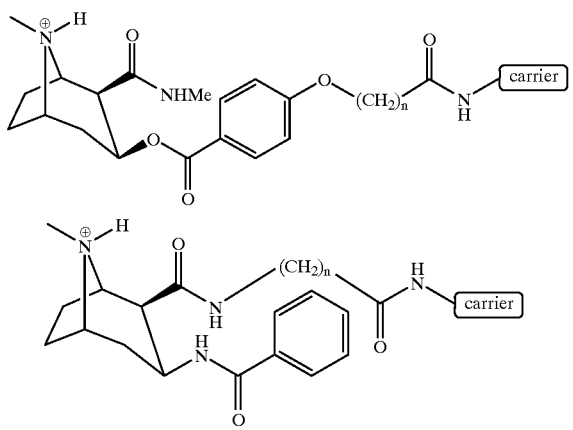

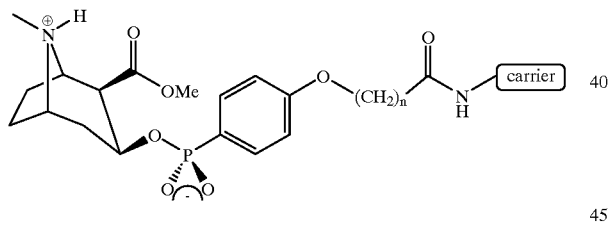

wherein n and m are integers from 2 to 8;
  isolating an anti-cocaine antibody producing cell from said subject which expresses said monoclonal antibody and cloning said cell; and
  isolating said monoclonal antibody produced by said cloned cell.

22. The method of claim 21, wherein said compound has the following formula:

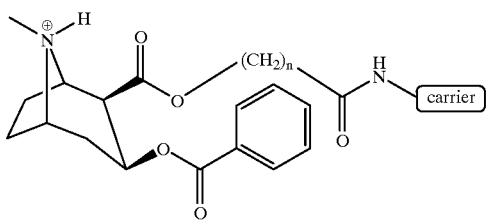

wherein n is an integer from 2 to 8.

23. The method of claim 22, wherein in said compound n is an integer from 4 to 6.

24. The method of claim 23, wherein in said compound n is 5.

25. A method of suppressing psychoactive effects of cocaine within a subject, said method comprising:

administering an anti-cocaine vaccine to said subject, said anti-cocaine vaccine comprising an injectable sterile solvent and an immunogenic amount of a compound having a formula selected from the group consisting of:

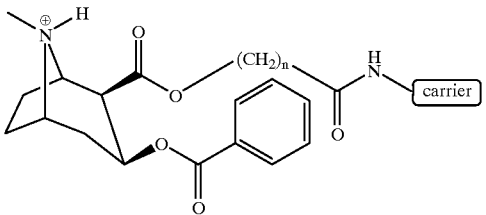

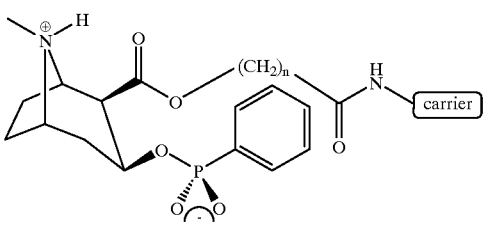

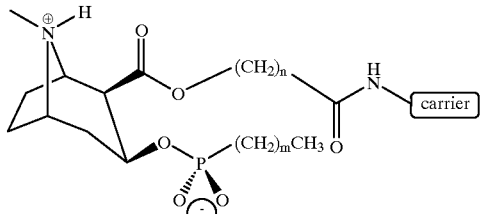

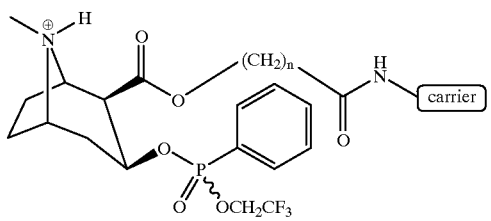

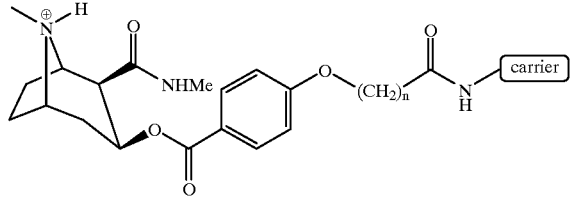

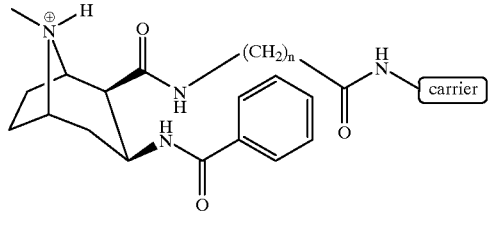

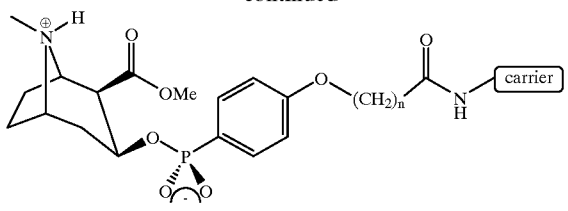
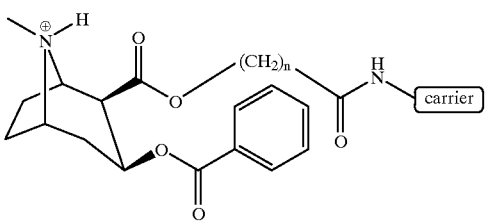
wherein n and m are integers from 2 to 8;
whereby antisera to cocaine is produced resulting in the suppression of the psychoactive effects to cocaine.
26. The method of claim 25, wherein said compound has the following formula:
wherein n is an integer from 2 to 8.
27. The method of claim 26, wherein in said compound n is an integer from 4 to 6.
28. The method of claim 27, wherein in said compound n is 5.
* * * * *

UNITED STATES PATENT AND TRADEMARK OFFICE
CERTIFICATE OF CORRECTION

PATENT NO. : 6,383,490 B1
DATED : May 7, 2002
INVENTOR(S) : Wirsching, Peter et al.

It is certified that error appears in the above-identified patent and that said Letters Patent is hereby corrected as shown below:

<u>Column 1,</u>
Line 2, under the title please add the following:

-- GOVERNMENT RIGHTS
This invention was made with government support Contract No. 3-5-90585 by the National Institutes of Health. The United States Government has certain rights in this invention. --

Signed and Sealed this

Twentieth Day of August, 2002

Attest:

JAMES E. ROGAN
Attesting Officer
Director of the United States Patent and Trademark Office